United States Patent
Goil et al.

(10) Patent No.: US 11,806,536 B2
(45) Date of Patent: Nov. 7, 2023

(54) METHOD AND DEVICE FOR MANAGING HIS BUNDLE PACING IN A NON-TRACKING MODE DURING AF/AT

(71) Applicant: Pacesetter, Inc., Sylmar, CA (US)

(72) Inventors: Aditya Goil, Stevenson Ranch, CA (US); Xiaoyi Min, Ventura, CA (US); Wenwen Li, San Jose, CA (US); Yun Qiao, Sunnyvale, CA (US); Jan O. Mangual-Soto, Rho (IT); Carin Folman, Bedford, MA (US)

(73) Assignee: Pacesetter, Inc., Sylmar, CA (US)

( * ) Notice: Subject to any disclaimer, the term of this patent is extended or adjusted under 35 U.S.C. 154(b) by 224 days.

(21) Appl. No.: 17/014,007

(22) Filed: Sep. 8, 2020

(65) Prior Publication Data
US 2022/0072303 A1  Mar. 10, 2022

(51) Int. Cl.
*A61N 1/365* (2006.01)
*A61B 5/00* (2006.01)
*A61N 1/05* (2006.01)
*A61B 5/283* (2021.01)

(52) U.S. Cl.
CPC .............. *A61N 1/365* (2013.01); *A61B 5/283* (2021.01); *A61B 5/686* (2013.01); *A61N 1/056* (2013.01)

(58) Field of Classification Search
CPC ................................ A61N 1/365; A61N 1/056
USPC .......................................................... 607/17
See application file for complete search history.

(56) References Cited

U.S. PATENT DOCUMENTS

2019/0022378 A1*  1/2019  Prillinger ............. A61N 1/0565

* cited by examiner

*Primary Examiner* — Nicole F Lavert
(74) *Attorney, Agent, or Firm* — THE SMALL PATENT LAW GROUP LLC; Dean D. Small

(57) ABSTRACT

System and methods are provided herein and include a HIS electrode configured to be located proximate to a HIS bundle and to at least partially define a HIS sensing vector. They system includes memory to store program instructions and cardiac activity (CA) signals for a series of beats utilizing a candidate sensing configuration. The candidate sensing configuration is defined by i) the HIS sensing vector and ii) a sensing channel that utilizes sensing circuitry configured to operate based on one or more sensing settings to detect near field and far field activity. The system includes one or more processors that, when executing the program instructions, are configured to analyze the CA signals to obtain an atrial (A) feature of interest (FOI) and a ventricular (V) FOI for the corresponding beats within the series of beats and identify a V-A FOI relation between the A FOIs and the V FOIs across the series of beats. The system adjusts the candidate sensing configuration and repeat the obtain, analyze and identify operations to obtain a collection of V-A FOI relations for a corresponding collection of candidate sensing configurations and selects a resultant sensing configuration from the collection of candidate sensing configurations based on one or more criteria, the resultant sensing configuration to be utilized to manage HIS bundle pacing during an atrial arrhythmia.

24 Claims, 9 Drawing Sheets

METHOD AND DEVICE FOR MANAGING HIS BUNDLE PACING IN A NON-TRACKING MODE DURING AF/AT

BACKGROUND

Embodiments of the present disclosure generally relate to HIS bundle pacing and more specifically, to managing HIS bundle pacing in the presence of an atrial arrhythmia while an IMD is switched to a non-tracking mode.

In a normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (AV) node and a ventricular conduction system comprised of the bundle of HIS (also referred to as the HIS bundle), the left and right bundle branches, and the Purkinje fibers, causing a depolarization and the resulting ventricular chamber contractions. The depolarization of the interventricular septum and ventricles is generally referred to as a QRS complex and is observed and measured through the use of electrocardiograms (ECGs) and similar equipment for measuring electrical activity of the heart.

Direct stimulation of the HIS bundle has been found to provide hemodynamic improvement for various patients including those suffering from dilated cardiomyopathy but having normal ventricular activation. Other examples of patients that may benefit from direct stimulation of the HIS bundle include those with atrioventricular junction (AVJ) ablation or third-degree AV block that require permanent ventricular pacing. Accordingly, the natural conduction system, when intact, can provide hemodynamically optimal depolarization timing of the heart chambers.

However, an opportunity remains to improve upon HIS bundle pacing methods and systems. In some patients, the HIS sensing channel experiences an unduly high incidence of atrial signal over-sensing (e.g. declaring atrial activity in coming over a HIS sensing channel to represent a ventricular event). Methods and systems have been proposed to avoid atrial over sensing. As one example, an atrial over sensing avoidance (AOA) process utilizes a timing of an atrial sensed or atrial paced event marker to start a timing window (e.g. an AOA window). The AOA process analyzes incoming signals during the AOA window for atrial activity components. Based on the analysis, the AOA process adjust a ventricular event sensitivity profile utilized by the sensing channel to avoid atrial over sensing.

The foregoing AOA methods and systems experience certain limitations. For example, the AOA process positions and AOA window over incoming CA signals, wherein the window position is located relative to an atrial paced or sensed event marker. However, during automatic mode switching (AMS), the implantable medical device switches to a non-tracking mode that no longer tracks atrial activity. Without atrial tracking, the foregoing AOA methods and systems are unable to identify the atrial sensed/pace marker, and consequently, the foregoing AOA process may be disabled temporarily while in the non-tracking mode. When the foregoing AOA process is disabled, the potential exists that over sensing of atrial activity could arise while a patient is experiencing an atrial arrhythmia, such as atrial fibrillation (AF) or atrial tachycardia (AT). When atrial events are over sensed during AF or AT, the implantable device may inadvertently inhibit HIS pacing, when HIS bundle pacing is otherwise desired.

A need remains for methods and devices that overcome the foregoing and other disadvantages of conventional approaches.

SUMMARY

In accordance with embodiments herein, methods and systems are described that provide detective ventricular events over a HIS sensing channel and avoid atrial over sensing while in the presence of an arrhythmia, such as AF or AT.

In accordance with embodiments herein, a system is provided. The system includes a HIS electrode configured to be located proximate to a HIS bundle and to at least partially define a HIS sensing vector. They system includes memory to store program instructions and cardiac activity (CA) signals for a series of beats utilizing a candidate sensing configuration. The candidate sensing configuration is defined by i) the HIS sensing vector and ii) a sensing channel that utilizes sensing circuitry configured to operate based on one or more sensing settings to detect near field and far field activity. The system includes one or more processors that, when executing the program instructions, are configured to analyze the CA signals to obtain an atrial (A) feature of interest (FOI) and a ventricular (V) FOI for the corresponding beats within the series of beats and identify a V-A FOI relation between the A FOIs and the V FOIs across the series of beats. The system adjusts the candidate sensing configuration and repeat the obtain, analyze and identify operations to obtain a collection of V-A FOI relations for a corresponding collection of candidate sensing configurations and selects a resultant sensing configuration from the collection of candidate sensing configurations based on one or more criteria, the resultant sensing configuration to be utilized to manage HIS bundle pacing during an atrial arrhythmia.

Optionally, the one or more processors may be further configured to determine an A boundary for the A FOIs over the series of beats and a V boundary for the V FOIs over the series of beats. The one or more processors may be further configured to determine a lowest value of the V FOIs collected over the series of beats, and an upper value of the A FOIs collected over the series of beats. The identify operation may further comprise determining whether a ratio of the lowest value of the V FOIs and the upper value of the A FOIs exceed a predetermined threshold. The one or more processors may be further configured to identify the V-A FOI relation by calculating a relation between at least one of means, means plus standard deviations, amplitudes or standard deviations between the V FOI and the A FOI.

Optionally, the one or more processors may be further configured to determine a ventricular sensitivity based on the resultant sensing configuration and may configure an implantable medical device to, during a non-tracking mode, utilize the ventricular sensitivity to detect ventricular events from the CA signals collected over the HIS sensing vector and a HIS sensing channel. The implantable medical device may not time HIS bundle pacing based on atrial paced or sensed events during the non-tracking mode. The one or more processors may be further configured to implement a verification process to verify the resultant sensing configuration in parallel with an atrial oversensing avoidance (AOA) process. The HIS electrode may be configured to be located in one of a right atrium or right ventricle proximate to the HIS bundle.

Optionally, the system may comprise an implantable medical device (IMD). The IMD may include a header configured to be coupled to a lead having the HIS electrode located proximate to a distal end of the lead. The IMD may include IMD memory and an IMD processor. The IMD memory may be configured to store the resultant sensing configuration. The IMD processor may be configured to utilize the resultant sensing configuration to manage HIS bundle pacing during the atrial arrhythmia. The IMD processor may be further configured to determine a ventricular sensitivity based on the resultant sensing configuration and may operate in a non-tracking mode that utilizes the ventricular sensitivity to detect ventricular events from the CA signals collected over the HIS sensing vector and a HIS sensing channel and when in the non-tracking mode, wherein the HIS bundle pacing is not timed based on atrial paced or sensed events.

In accordance with embodiments herein, an implantable medical device (IMD) is provided. The IMD includes a lead having a HIS electrode configured to be located proximate to a HIS bundle to at least partially define a HIS sensing vector and memory to store program instructions. The IMD includes sensing circuitry configured to define a sensing channel and to be coupled to the HIS electrode to collect cardiac activity (CA) signals for a series of beats utilizing a candidate sensing configuration. The candidate sensing configuration is defined by i) the HIS sensing vector and ii) the sensing channel. The IMD includes one or more processors that, when executing the program instructions, are configured to analyze the CA signals to obtain an atrial (A) feature of interest (FOI) and a ventricular (V) FOI for the corresponding beats within the series of beats and identify a V-A FOI relation between the A FOIs and the V FOIs across the series of beats. The IMD adjusts the candidate sensing configuration and repeat the obtain, analyzes and identifies operations to obtain a collection of V-A FOI relations for a corresponding collection of candidate sensing configurations and selects a resultant sensing configuration from the collection of candidate sensing configurations based on one or more criteria, the resultant sensing configuration to be utilized to manage HIS bundle pacing during an atrial arrhythmia.

Optionally, the one or more processors may be further configured to determine an A boundary for the A FOIs over the series of beats and a V boundary for the V FOIs over the series of beats. The one or more processors may be further configured to determine a lowest value of the V FOIs collected over the series of beats, and an upper value of the A FOIs collected over the series of beats. The identify operation may further comprise determining whether a ratio of the lowest value of the V FOIs and the upper value of the A FOIs exceed a predetermined threshold. The one or more processors may be further configured to identify the V-A FOI relation by calculating a relation between at least one of means, means plus standard deviations, amplitudes or standard deviations between the V FOI and the A FOI.

In accordance with embodiments herein, a method for managing HIS bundle pacing using an implantable medical device (IMD). The method obtains cardiac activity (CA) signals for a series of beats utilizing a candidate sensing configuration. The candidate sensing configuration is defined by i) a HIS sensing vector that utilizes at least one HIS electrode and ii) a sensing channel that utilizes sensing circuitry configured to operate based on one or more sensing settings to detect near field and far field activity. The method analyzes the CA signals to obtain an atrial (A) feature of interest (FOI) and a ventricular (V) FOI for the corresponding beats within the series of beats and identifies a V-A FOI relation between the A FOIs and the V FOIs across the series of beats. The method adjusts the candidate sensing configuration and repeats the obtaining, analyzing and identifying to obtain a collection of V-A FOI relations for a corresponding collect of candidate sensing configurations. The method selects a resultant sensing configuration from the collection of candidate sensing configurations based on one or more criteria and utilizes the resultant sensing configuration to manage HIS bundle pacing during an atrial arrhythmia.

Optionally, the method may determine an A boundary for the A FOIs over the series of beats and a V boundary for the V FOIs over the series of beats. The determining may further comprise determining a lowest value of the V FOIs collected over the series of beats, and an upper value of the A FOIs collected over the series of beats, the identifying the V-A FOI relation further comprising determining whether a ratio of the lowest value of the V FOIs and the upper value of the A FOIs exceed a predetermined threshold. The identifying the V-A FOI relation may include calculating a relation between at least one of means, means plus standard deviations, amplitudes or standard deviations between the V FOI and the A FOI.

Optionally, the method may determine a ventricular sensitivity based on the resultant sense configuration; and, during a non-tracking mode, may utilize the ventricular sensitivity to detect ventricular events from the CA signals collected over the HIS sensing vector and a HIS sensing channel. The IMD may not time HIS bundle pacing based on atrial paced or sensed events during the non-tracking mode. The method may implement a verification process to verify the resultant sensing configuration in parallel with an atrial oversensing avoidance (AOA) process. The method may locate the at least one HIS electrode in one of a right atrium or right ventricle proximate to the HIS bundle.

BRIEF DESCRIPTION OF THE DRAWINGS

FIG. 8 illustrates a functional block diagram of the external device 800 that is operated in accordance with the

DETAILED DESCRIPTION

Figure 1:
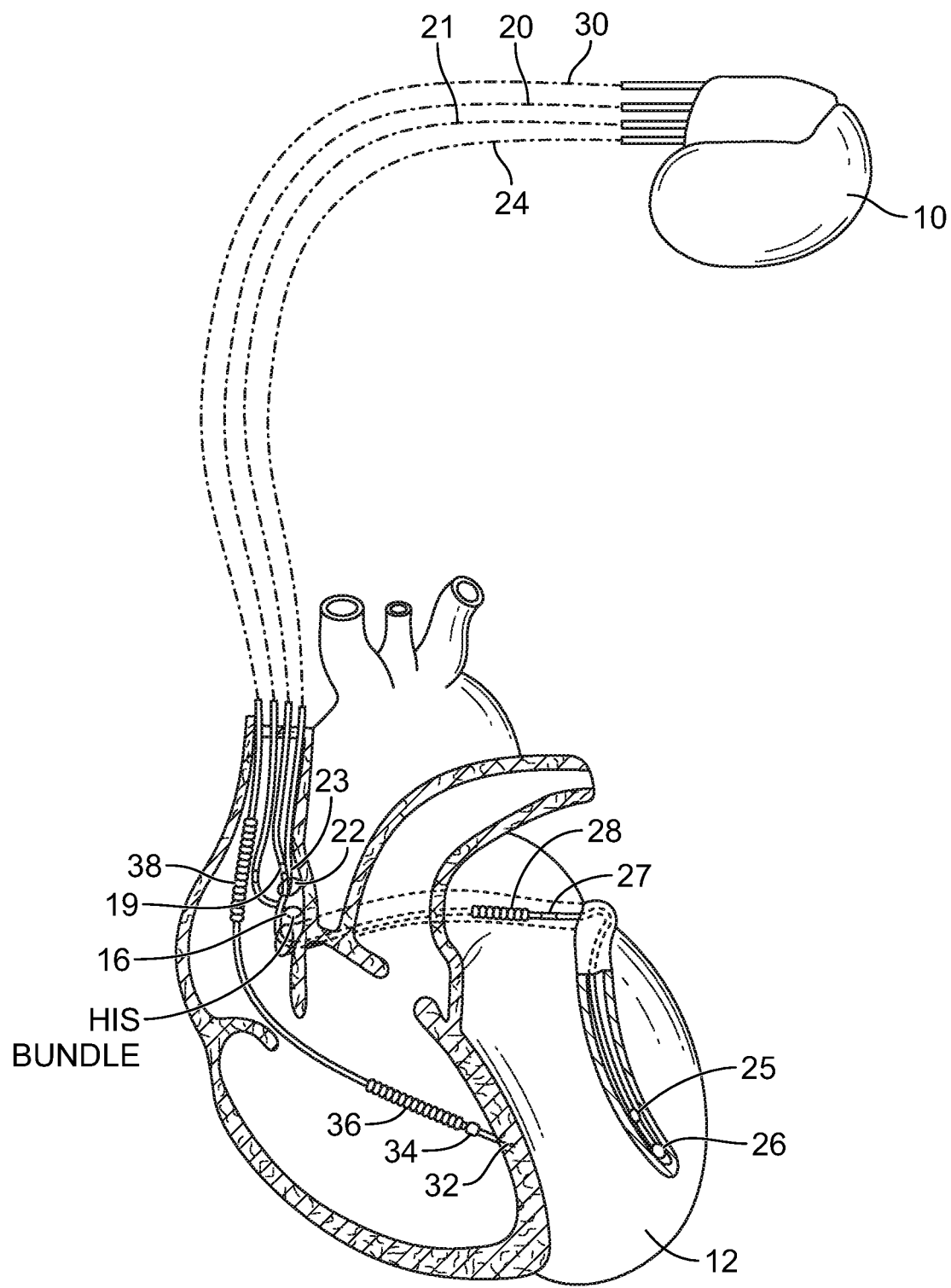
FIG. 1 illustrates an implantable medical device in electrical communication with a patient's heart by way of one or more of four leads and suitable for delivering multi-chamber stimulation.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. By way of example, one or more operations of each method described herein may be implemented by one or more processors or circuitry of an implantable medical device, while one or more other operations of the methods described herein may be implemented by one or more processors of an external device, such as a local external device, clinician programmer and/or a remote server. While the operations of some methods may be described as performed by the processor(s) of one device, additionally, some or all of such operations may be performed by the processor(s) of another device described herein.

The terms "atrial tracking mode" and "tracking mode" refer to a mode of operation in which the IMD analyzes cardiac activity signals collected over an atrial sensing channel to identify atrial events (e.g. sensed or paced) and utilizes the sensed or paced atrial event to set one or more timing windows and/or search windows are utilized to monitor for other events of interest.

The term "non-tracking mode" refers to a mode of operation in which the implantable medical device does not identify atrial paced or sensed events from an analysis of CA signals collected over an atrial sensing channel and the device does not time HIS bundle pacing based on atrial paced or sensed events. Instead, during the non-tracking mode, HIS bundle pacing is based on preprogrammed timing cycles. For example, during a VVI mode, each initiated timing cycle corresponds to the VH delay. During the DDI mode, ventricular-HIS (VH) timing is utilized for HIS pacing, and a HIS-atrium (HA) timing is utilized for atrial pacing.

The term "atrial over sensing" refers to a condition in which cardiac activity signals incoming over the HIS sensing channel are labeled as ventricular activity, even though the cardiac activity signals are associated with atrial activity.

The terms "cardiac activity signal", "cardiac activity signals", "CA signal" and "CA signals" (collectively "CA signals") are used interchangeably throughout to refer to an analog or digital electrical signal recorded by two or more electrodes positioned subcutaneous or cutaneous, where the electrical signals are indicative of cardiac electrical activity. The cardiac activity may be normal/healthy or abnormal/arrhythmic. Non-limiting examples of CA signals include ECG signals collected by cutaneous electrodes, and EGM signals collected by subcutaneous electrodes.

The term "real-time" refers to a time frame contemporaneous with a normal or abnormal episode occurrences. For example, a real-time process or operation would occur during or immediately after (e.g., within minutes or seconds after) a cardiac event, a series of cardiac events, an arrhythmia episode, and the like.

The term "sensitivity profile" refers to a set of sensitivity parameters that define a sensitivity level. In some embodiments, a sensitivity profile may represent a straight line sensitivity level that does not change over the course of time. Alternatively, a sensitivity profile may be more complex as defined by sensitivity parameters. Nonlimiting examples of sensitivity parameters include a sensitivity limit, starting sensitivity level, ending sensitivity level, decay delay, slope of sensitivity decay and the like. Examples of sensitivity profiles and adjustments therein are described in the co-pending '351 application.

The term "sensitivity level", as used herein, refers to a threshold that an input CA signal must exceed for an implantable device to identify a CA signal feature of interest (e.g., an AOE, a P-wave, an R-wave). As one non-limiting example, software may be implemented using a programmed sensitivity level to declare an R-wave to be detected when the input CA signal exceeds the current programmed sensitivity level In response, the software declares a device documented feature (e.g., R-wave) marker.

The terms "far field signal" and "FF signal" shall mean a signal, that is detected by a sensing electrode(s) located in or immediately adjacent one chamber of the heart, but where the signal originated in another chamber of the heart or outside of the heart. For example, a HIS electrode located in the RV proximate to the HIS bundle may detect, as far field signals, signals originating from the right atrium, left atrium or left ventricle. As another example, an RA electrode located in the right atrium may detect, as far field signals, signals originating outside of the right atrium, such as from the right ventricle, left atrium or left ventricle.

The terms "near field signal" and "in an effort signal" shall mean a signal that originates from a chamber of the heart and is detected by a sensing electrode(s) located in or immediately adjacent the same chamber of the heart. For example, the HIS electrode located in the RV proximate to the HIS bundle may detect, as a near field signal, signals originating from the right ventricle. As another example, an RA electrode located in the right atrium may detect, as near field signals, signals originating from the right atrium.

The term "obtain" or "obtaining", as used in connection with data, signals, information and the like, includes at least one of i) accessing memory of an external device or remote server where the data, signals, information, etc. are stored, ii) receiving the data, signals, information, etc. over a wireless communications link between the S-IMD and a local external device, and/or iii) receiving the data, signals, information, etc. at a remote server over a network connection. The obtaining operation, when from the perspective of an S-IMD, may include sensing new signals in real time, and/or accessing memory to read stored data, signals, information, etc. from memory within the S-IMD. The obtaining operation, when from the perspective of a local external device, includes receiving the data, signals, information, etc. at a transceiver of the local external device where the data, signals, information, etc. are transmitted from an S-IMD and/or a remote server. The obtaining operation may be from the perspective of a remote server, such as when receiving the data, signals, information, etc. at a network interface from a local external device and/or directly from an S-IMD. The remote server may also obtain the data, signals, information, etc. from local memory and/or from other memory, such as within a cloud storage environment and/or from the memory of a workstation or clinician external programmer. The obtaining operation, when from the perspective of a PIMD, may include sensing new signals in real time, and/or accessing memory to read stored data, signals, information, etc. from memory within the IMD. The obtaining operation, when from the perspective of a local external device, includes receiving the data, signals, information, etc. at a transceiver of the local external device where the data, signals, information, etc. are transmitted from a PIMD and/or a remote server. The obtaining operation may be from the perspective of a remote server, such as when receiving the data, signals, information, etc. at a network interface from a local external device and/or directly from a PIMD. The remote server may also obtain the data, signals, information, etc. from local memory and/or from other memory, such as within a cloud storage environment and/or from the memory of a workstation or clinician external programmer.

Embodiments may be implemented in connection with one or more implantable medical devices (IMDs). Non-limiting examples of IMDs include one or more of a cardiac monitoring device, pacemaker, cardioverter, cardiac rhythm management device, defibrillator, neurostimulator, leadless monitoring device, leadless pacemaker and the like.

Additionally or alternatively, the IMD may be a leadless implantable medical device (LIMD) that include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

Additionally or alternatively, the IMD may be a subcutaneous IMD that includes one or more structural and/or functional aspects of the device(s) described in U.S. application Ser. No. 15/973,195, titled "Subcutaneous Implantation Medical Device With Multiple Parasternal-Anterior Electrodes" and filed May 7, 2018; U.S. application Ser. No. 15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entireties. Further, one or more combinations of IMDs may be utilized from the above incorporated patents and applications in accordance with embodiments herein.

Additionally or alternatively, embodiments herein may be implemented by, or in connection with, the systems and methods described in U.S. Patent Application 2019/0022378, titled "Systems and Methods for Automated Capture Threshold Testing and Associated HIS Bundle Pacing", published Jan. 24, 2019, and/or U.S. patent application Ser. No. 15/973,351, titled "METHOD AND SYSTEM TO DETECT R-WAVES IN CARDIAC ARRHYTHMIC PATTERNS"; U.S. application Ser. No. 16/904,837, filed Jun. 18, 2020, titled "SYSTEMS AND METHODS FOR IMPROVED HIS BUNDLE AND BACKUP PACING TIMING", the complete subject matter of which are incorporated herein by reference in their entireties.

Additionally or alternatively, embodiments herein may be implemented by, or in connection with, the systems and methods described in U.S. application Ser. No. 16/904,837, Titled "SYSTEMS AND METHODS FOR IMPROVED HIS BUNDLE AND BACKUP PACING TIMING", filed Jun. 18, 2020; U.S. application Ser. No. 16/871,166, Titled "SYSTEMS AND METHODS FOR IMPROVED HIS BUNDLE AND BACKUP PACING TIMING", filed May 11, 2020; U.S. Provisional Application 62/875,863, Titled "SYSTEMS AND METHODS FOR IMPROVED HIS BUNDLE AND BACKUP PACING TIMING", filed Jul. 18, 2019; U.S. application Ser. No. 16/181,234, Titled "AUTOMATED OPTIMIZATION OF HIS BUNDLE PACING FOR CARDIAC RESYNCHRONIZATION THERAPY", filed Nov. 5, 2018; U.S. application Ser. No. 16/138,766, Titled "SYSTEMS AND METHODS FOR AUTOMATED CAPTURE THRESHOLD TESTING AND ASSOCIATED HIS BUNDLE PACING", filed Sep. 21, 2018; U.S. application Ser. No. 15/653,357, Titled "SYSTEMS AND METHODS FOR AUTOMATED CAPTURE THRESHOLD TESTING AND ASSOCIATED HIS BUNDLE PACING", filed Jul. 18, 2017; U.S. Provisional Application 62/948,047, Titled "AUTOMATIC PACING IMPULSE CALIBRATION USING PACING RESPONSE TRANSITIONS", filed Dec. 13, 2019; and U.S. Provisional Patent Application No. 62/902,698, filed Sep. 19, 2019 and titled "METHOD AND DEVICE FOR AVOIDING ATRIAL ACTIVITY OVERSENSING ON HIS SENSING CHANNEL, the complete subject matter of which are incorporated herein by reference in their entireties.

The '698 provisional application describes methods and systems that utilize an atrial over sensing avoidance period (AOAP) to avoid atrial over sensing events (AOE) over a HIS sensing channel. The AOAP process utilizes a timing of atrial sensed or paced markers to start a time window that covers an intra-atrial conduction delay (IACT). The AOAP process determines if an AOE is present over the HIS sensing channel and seeks to identify settings to avoid the AOE.

In accordance with new and unique aspects herein, methods and systems are disclosed that are configured to operate in connection with AOAP methods and systems (e.g., as described in the 698 provisional application). In accordance with embodiments herein, methods and systems are described to sense ventricular events over the HIS sensing channel during AF or AT while avoiding atrial over sensing. In accordance with new and unique aspects herein, embodiments are described to select between a collection of HIS (primary) sensing configurations and secondary sensing configurations. The process to select from the collection of HIS sensing configurations iteratively steps between multiple narrowband HIS sensing configurations and multiple wideband sensing configurations and collects features and data in connection with each narrowband and wideband sensing configuration. The features/data are then compared across configurations and, based on the comparison, the process identifies select/resultant HIS and secondary sensing configurations that meet certain criteria of interest, such as a ratio between amplitudes of ventricular events and amplitudes of atrial events. Additionally or alternatively, parameters of a wideband sensing channel may be adjusted to obtain a desired (e.g. optimized) feature differentiation between A and V events.

Additionally or alternatively, embodiments herein assess the extracted features from the HIS/primary & secondary sensing configurations. For example, an in-clinic sense test may be implemented in which sinus rhythm is sensed uses the AOAP sensing algorithm identification of V sensing events as the standard for comparison. The results from the AOAP sensing algorithm are compared to the performance of the feature-based V sensed event classified, described herein, using the extracted features from the narrowband and the wideband signals. Upon a successful comparison, an extracted feature template is saved for future operation during AMS.

Additionally or alternatively, during day-to-day use, the methods and IMDs herein sense ventricular activity during a non-tracking mode, in which atrial events are not identified from CA signals collected over an atrial sensing channel (e.g. in connection with an RA sensing vector). Embodiments implement the non-tracking mode while sensing ventricular events and rejecting atrial oversensing over the HIS sensing channel. For example, upon entering a non-tracking mode, the IMD begins monitoring the wideband channel and extracting features for each beat. The extracted features are compared to a feature template. When a match occurs, the IMD classifies the event as a V sensed event and triggers the non-tracking mode timing cycles.

System Overview

FIG. 1 illustrates a stimulation device 10 in electrical communication with a patient's heart 12 by way of one or more of four leads, 20, 21, 24, and 30 and suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage or atrial septum. To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode within the coronary veins overlying the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus which overlies the left ventricle. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. In another embodiment, an additional electrode for providing left ventricular defibrillation shocking therapy may be included in the portion of the lead overlying the left ventricle, adjacent to the ring electrode 25. The stimulation device 10 is also shown in electrical communication with the patient's heart 12 by way of an implantable right ventricular lead 30 having, in this embodiment, a right ventricular tip electrode 32, a right ventricular ring electrode 34, a right ventricular coil electrode 36, and a superior vena cava (SVC) coil electrode 38. Typically, the right ventricular lead 30 is transvenously inserted into the heart 12 so as to place the right ventricular tip electrode 32 in the right ventricular apex so that the right ventricular coil electrode 36 will be positioned in the right ventricle and the SVC coil electrode 38 will be positioned in the superior vena cava. Accordingly, the right ventricular lead 30 is capable of receiving cardiac signals and delivering stimulation in the form of pacing and shock therapy to the right ventricle.

The stimulation device 10 is further connected to a HIS bundle lead 21 having a HIS tip electrode 16, such as a helical active fixation device, and a HIS ring electrode 19 located proximal from the HIS tip electrode 16. In certain implementations, the HIS ring electrode 19 is located approximately 10 mm proximal the HIS tip electrode 16. The HIS bundle lead 21 may be transvenously inserted into the heart 12 so that the HIS tip electrode 16 is positioned in the tissue of the HIS bundle. The HIS bundle lead 21 may be located proximate the HIS bundle in the RA or in the RV. Accordingly, the HIS bundle lead 21 is capable of receiving depolarization signals propagated in the HIS bundle or delivering stimulation to the HIS bundle, creating a depolarization that can be propagated through the lower conductive pathways of the right and left ventricles (i.e., the right and left bundle branches and Purkinje fibers).

Figure 2:
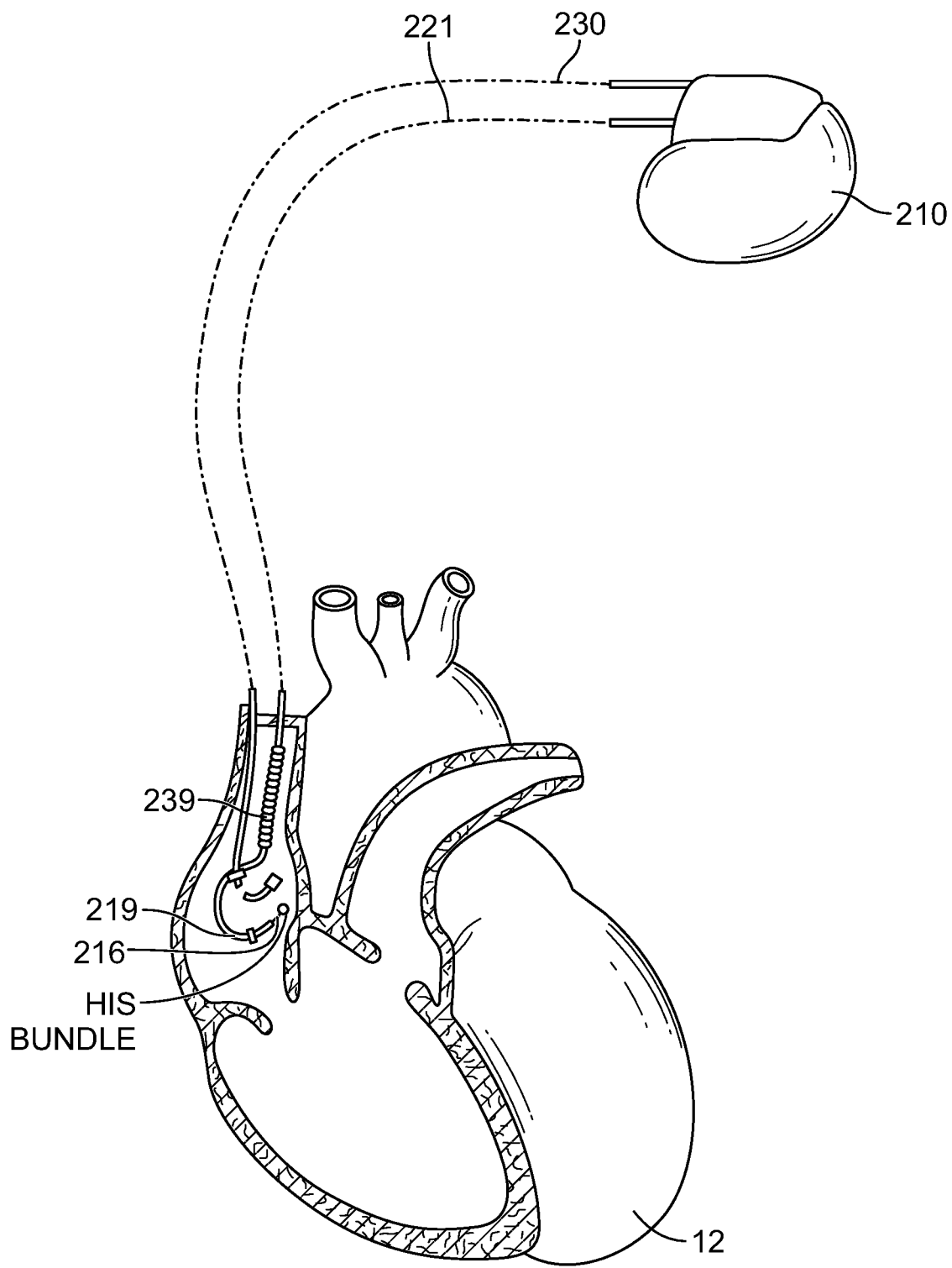
FIG. 2 illustrates a dual chamber implantable medical device in communication with one atrium, one ventricle, and the HIS bundle in accordance with embodiments herein.

An alternative embodiment of the present disclosure is shown in FIG. 2 in which a dual chamber stimulation device 210 is in communication with one atrium, one ventricle, and the HIS bundle. Though not explicitly illustrated in FIG. 2, a right atrial lead 20 can be optionally included. In such implementations, the stimulation device 210 maintains communication with the right atrium of the heart 12 via a right atrial lead 20 having at least an atrial tip electrode 22 and an atrial ring electrode 23, and an SVC coil electrode 239. A HIS bundle lead 221, having a HIS tip electrode 216 and a HIS ring electrode 219, is positioned such that the HIS tip electrode 216 is proximate the HIS bundle tissue. The stimulation device 210 is shown in FIG. 2 in electrical communication with the patient's heart 12 by way of a right ventricular lead 230 including a right ventricular tip electrode 232, a right ventricular ring electrode 234, and a right ventricular coil electrode 236.

Optionally, the distal end of the HIS bundle lead 21 is further provided with a non-traumatic conductive surface (also referred to herein interchangeably as a mapping collar). The non-traumatic conductive surface is advantageously used to make electrical measurements that indicate the location of the HIS bundle without having to anchor the HIS bundle tip electrode 16 into the endocardial tissue. The non-traumatic conductive surface and the HIS bundle tip electrode 16 are electrically coupled within the lead body of the HIS bundle lead 21 and together form one conductive element for the purposes of sensing, stimulation, and impedance measurements. Drugs, for example an acute antiarrhythmic drug such as lidocaine and/or an anti-inflammatory agent such as dexamethasone sodium phosphate, can be stored, for example, within a reservoir (not shown) at the base of the HIS bundle tip electrode 16 for local dispensation.

The HIS bundle lead 21 is also provided with a HIS ring electrode 19. The HIS ring electrode 19 is preferably spaced between approximately 2 mm and 30 mm, but preferably 10 mm, from the HIS tip electrode 16. The HIS ring electrode 19 may function as the return electrode during bipolar sensing, stimulation or impedance measurement operations.

The HIS tip electrode 16 and the HIS ring electrode 19 are each connected to flexible conductors respectively, which may run the entire length of the HIS bundle lead 21. The flexible conductor is connected to the HIS tip electrode 16 and is electrically insulated from the flexible conductor by a layer of insulation. The conductor is connected to the HIS ring electrode 19. The flexible conductors serve to electrically couple the HIS ring electrode 19 and the HIS tip electrode 16 to the HIS ring electrode terminal 51 and the HIS tip electrode terminal 50, respectively. One embodiment of the HIS bundle lead 21 is available from St. Jude Medical CRMD as lead model No. 1488T.

As explained herein, in accordance with new and unique aspects herein, different sensing configurations are tested to identify sensing vectors and sensing channel parameters that are able to reliably distinguish between atrial and ventricular features of interest, sufficient to identify ventricular events with a high degree of confidence, without a need for atrial tracking. For example, a first sensing vector may be tested between the HIS ring electrode 19 and the atrial ring electrode, while a second sensing vector may be tested between the HIS tip electrode 16 and the atrial ring electrode. Optionally, a third sensing vector may be tested between the HIS ring electrode 19 and an atrial tip electrode. Additionally or alternatively, a sensing vector may be tested between the HIS ring and/or tip electrodes 19 and 16. Additionally or alternatively, the sensing vector may be tested between the HIS tip electrode 16 and/or HIS ring electrode 19 and one or more RV electrodes and/or one or more LV electrodes. Each combination of electrodes, as used to define a corresponding sensing vector, may be similarly switched between bipolar, unipolar and extended bipolar configurations.

In the examples of FIGS. 1 and 2, the HIS electrodes are illustrated as being located in the right atrium proximate to the HIS bundle. Optionally, the HIS electrodes may be provided on a lead that extends into the right ventricle, with the HIS electrodes positioned proximate to the HIS bundle, but positioned in the right ventricle. Additionally or alternatively, the HIS tip electrode 16 may be configured to include a helix or other mechanism to be burrowed into the septal wall within the right atrium proximate to the HIS bundle and/or proximate to the proximal end of the right bundle branch or proximal end of the left bundle branch. For example, the HIS electrode may be positioned as described in co-pending U.S. application Ser. No. 16/988,821, titled "SYSTEMS AND METHODS FOR MANAGING ATRIAL-VENTRICULAR DELAY ADJUSTMENTS" filed 10 Aug. 2020 (now U.S. Pat. No. 11,654,288, issued 23 May 2023), the complete subject matter of which is expressly incorporated herein by reference in its entirety.

Figure 3:
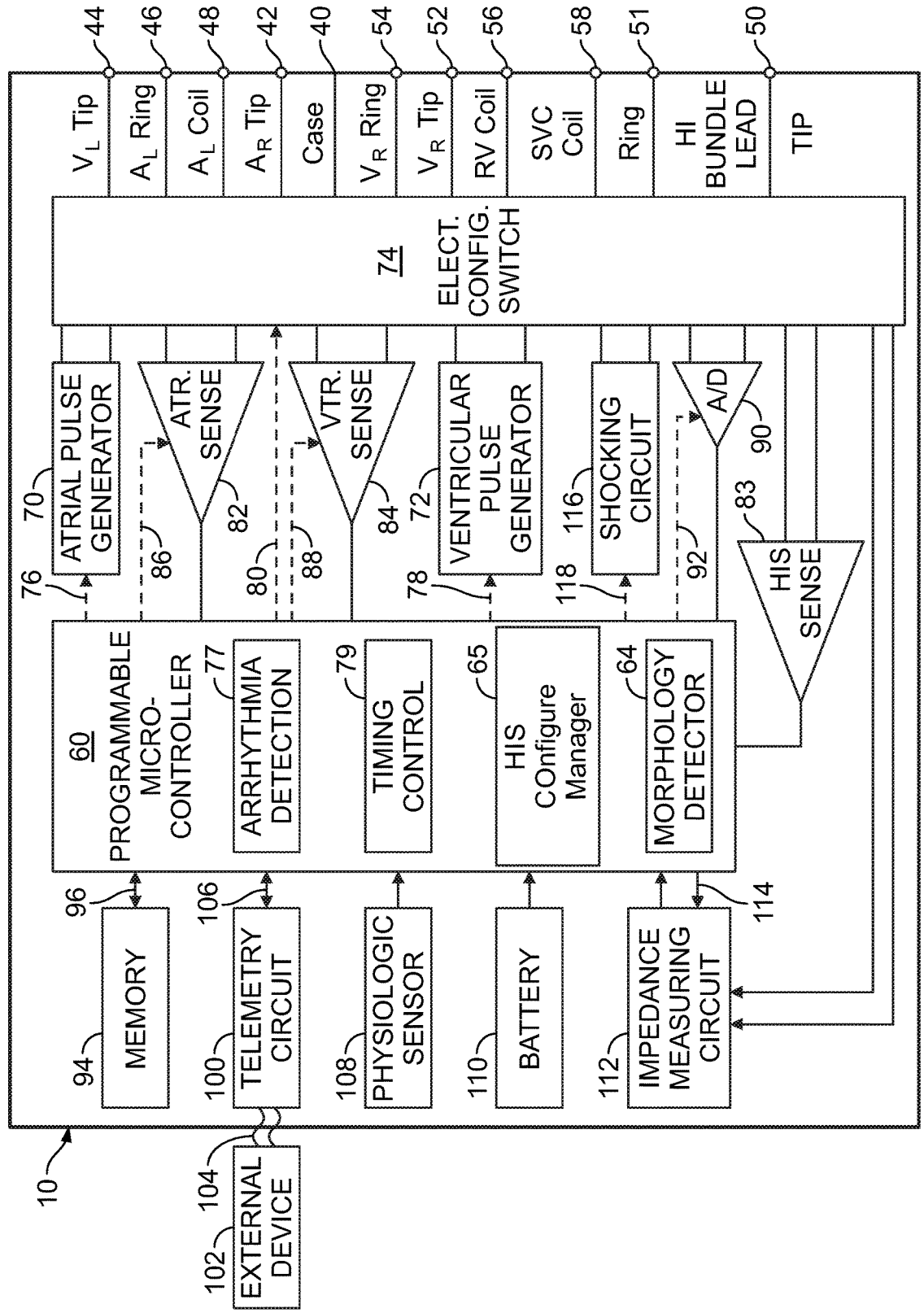
FIG. 3 illustrates a simplified block diagram of the implantable medical devices of FIGS. 1 and 2 in accordance with embodiments herein.

FIG. 3 illustrates a simplified block diagram of the multi-chamber implantable stimulation device 10 of FIG. 1, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chambers) with cardioversion, defibrillation and pacing stimulation. The housing 40 for the stimulation device 10, shown schematically in FIG. 3, is often referred to as the "can", "case" or "case electrode" and may be programmably selected to act as the return electrode for all "unipolar" modes. The housing 40 may further be used as a return electrode alone or in combination with one or more of the coil electrodes 28, 36, and 38 (shown in FIG. 1) for shocking purposes. The housing 40 further includes a connector (not shown) having a plurality of terminals 42, 44, 46, 48, 50-52, 54, 56, and 58 (shown schematically and, for convenience, next to the names of the electrodes to which they are connected). As such, to achieve right atrial sensing and pacing, the connector includes at least a right atrial tip terminal (AR TIP) 42 adapted for connection to the atrial tip electrode 22 (shown in FIG. 1).

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively (each shown in FIG. 1). To support right chamber sensing, pacing and shocking, the connector further includes a right ventricular tip terminal ($V_R$ TIP) 52, a right ventricular ring terminal ($V_R$ RING) 54, a right ventricular shocking terminal (RV COIL) 56, and an SVC shocking terminal (SVC COIL) 58, which are adapted for connection to the right ventricular tip electrode 32, right ventricular ring electrode 34, the right ventricular coil electrode 36, and the SVC coil electrode 38, respectively (each shown in FIG. 1). To achieve HIS bundle sensing, or sensing and stimulation, the connector further includes a HIS bundle lead tip terminal 50 and a HIS bundle lead ring terminal 51 which are adapted for connection to the HIS tip electrode 16 and the HIS ring electrode 19, respectively (each shown in FIG. 1).

At the core of the stimulation device 10 is a programmable microcontroller 60 which controls the various modes of stimulation therapy. The microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present disclosure. Rather, any suitable microcontroller 60 may be used that carries out the functions described herein.

As shown in FIG. 3, an atrial pulse generator 70 and a ventricular pulse generator 72 generate pacing stimulation pulses for delivery by the right atrial lead 20, the right ventricular lead 30, the coronary sinus lead 24, and/or the HIS bundle lead 21 via an electrode configuration switch 74.

It is understood that in order to provide stimulation therapy in each of the four chambers of the heart, the atrial and ventricular pulse generators 70, 72 may include dedicated, independent pulse generators, multiplexed pulse generators, or shared pulse generators. The pulse generators 70, 72 are controlled by the microcontroller 60 via appropriate control signals 76, 78, respectively, to trigger or inhibit the stimulation pulses. As used herein, the shape of the stimulation pulses is not limited to an exact square or rectangular shape, but may assume any one of a plurality of shapes which is adequate for the delivery of an energy pulse, packet, or stimulus.

The microcontroller 60 further includes timing control circuitry 79 which is used to control the timing of such stimulation pulses (e.g., pacing rate) as well as to keep track of the timing of refractory periods, blanking intervals, noise detection windows, evoked response windows, alert intervals, marker channel timing, etc., which is well known in the art. According to one embodiment of the present disclosure, timing control circuitry 79 also controls the onset and duration of a HIS signal sensing window during which a depolarization signal conducted through the AV node to the HIS bundle can be detected. Timing control circuitry 79 also controls a timing delay provided after a detected HIS signal detection, prior to the delivery of a right and/or left ventricular stimulation pulse. The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, cross-chamber, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits 82, 84 may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

According to one embodiment of the present disclosure, a HIS sensing circuit 83 is selectively coupled to the HIS bundle lead 21 (shown in FIG. 1) for detecting the presence of a conducted depolarization arising in the atria and conducted to the HIS bundle via the AV node. As used herein, each of the atrial sensing circuit 82, the ventricular sensing circuit 84, and the HIS sensing circuit 83, includes a discriminator, which is a circuit that senses and can indicate or discriminate the origin of a cardiac signal in each of the cardiac chambers. Each sensing circuit 82-84 preferably employs one or more low power, precision amplifiers with programmable gain and/or automatic gain control, bandpass filtering, and a threshold detection circuit to selectively sense the cardiac signal of interest. The automatic gain control enables the device 10 to deal effectively with the difficult problem of sensing the low amplitude signal characteristics of atrial or ventricular fibrillation. The outputs of the sensing circuits 82-84 are connected to the microcontroller 60 which, in turn, is able to trigger or inhibit the atrial and ventricular pulse generators 70, 72, respectively, in a demand fashion in response to the absence or presence of cardiac activity in the appropriate chambers of the heart. The atrial and ventricular sensing circuits 82, 84, in turn, receive control signals ever signal lines 86, 88, from the microcontroller 60 for purposes of controlling the gain, threshold, polarization charge removal circuitry (not shown), and the timing of any blocking circuitry (not shown) coupled to the inputs of the sensing circuits 82, 84.

For arrhythmia detection, the stimulation device 10 includes an arrhythmia detector 77 that utilizes the atrial and ventricular sensing circuits 82, 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (ND) data acquisition system 90 represented by an ND converter. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the HIS bundle lead 21, the coronary sinus lead 24, and the right ventricular lead 30 through the switch 74 to sample cardiac signals across any pair of desired electrodes.

In one embodiment, the data acquisition system 90 is coupled to microcontroller 60, or to other detection circuitry, for detecting a desired feature of the HIS bundle signal. In one embodiment, an averaging component is used to determine a sliding average of the HIS bundle signal during a HIS signal sensing window using known or available signal averaging techniques.

Advantageously, the data acquisition system 90 may be coupled to the microcontroller 60, or other detection circuitry, for detecting an evoked response from the heart 12 in response to an applied stimulus, thereby aiding in the detection of capture. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

The HIS sensing circuit 83 is connected to one or more HIS electrodes, to collectively define the HIS sensing channel that collects at least a portion of the CA signals. The atrial sensing circuit 82 is connected to one or more RA electrodes, to collectively define an RA sensing channel. The memory 94 is configured to store the CA signals obtained over the RA sensing channel and over the HIS sensing channel. The memory also is configured to store program instructions. The memory 94 is configured to store program instructions and cardiac activity (CA) signals for a series of beats utilizing a candidate sensing configuration, the candidate sensing configuration defined by i) the HIS sensing vector and ii) a sensing channel that utilizes sensing circuitry configured to operate based on one or more sensing settings to detect near field and far field activity.

The microcontroller 60, when executing the program instructions, is configured to implement a HIS configuration manager 65 that, among other things, analyze the CA signals to obtain an atrial (A) feature of interest (FOI) and a ventricular (V) FOI for the corresponding beats within the series of beats; identify a V-A FOI relation between the A FOIs and the V FOIs across the series of beats; adjust the candidate sensing configuration and repeat the obtain, analyze and identify operations to obtain a collection of V-A FOI relations for a corresponding collect of candidate sensing configurations; select a resultant sensing configuration from the collection of candidate sensing configurations based on one or more criteria, the resultant sensing configuration to be utilized to manage HIS bundle pacing during an atrial arrhythmia.

The HIS configuration manager 65 is further configured to determine an A boundary for the A FOIs over the series of beats and a V boundary for the V FOIs over the series of beats. Additionally or alternatively, the HIS configuration manager 65 is further configured to determine a lowest value of the V FOIs collected over the series of beats, and an upper value of the A FOIs collected over the series of beats, the identify operation further comprising determining whether a ratio of the lower value of the V FOIs and the upper value of the A FOIs exceed a predetermined threshold. Additionally or alternatively, the HIS configuration manager 65 is further configured to identify the V-A FOI relation by calculating a relation between at least one of means, means plus standard deviations, amplitudes or standard deviations between the V FOI and the A FOI. Additionally or alternatively, the HIS configuration manager 65 is further configured to determine a ventricular sensitivity based on the resultant sense configuration; and to configure the implantable medical device to, during a non-tracking mode, utilize the ventricular sensitivity to detect ventricular events from the CA signals collected over the HIS sensing vector and a HIS sensing channel, wherein the implantable medical device does not time HIS bundle pacing based on atrial paced or sensed events during the non-tracking mode. Additionally or alternatively, the HIS configuration manager 65 is further configured to implement a verification process to verify the resultant HIS sensing configuration in parallel with an atrial oversensing avoidance (AOA) process.

In the present example, the above operations are performed by an implantable medical device having a housing that includes the memory and the one or more processors, the housing configured to be coupled to the RA electrode and HIS electrode. Optionally, the IMD may have at least a portion of the one or more processors, while an external device has at least a portion of the one or more processors.

The IMD and external device both perform at least a portion of the identifying, calculating, analyzing, adjusting, monitoring and managing operations.

Advantageously, the operating parameters of the implantable device 10 may be non-invasively programmed into the memory 94 through a telemetry circuit 100 in telemetric communication with the external device 102, such as a programmer, trans-telephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiologic sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, stimulation delays, etc.) at which the atrial and ventricular pulse generators 70, 72 generate stimulation pulses.

A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. However, any suitable sensor may be used which is capable of sensing a physiological parameter which corresponds to the exercise state of the patient. The type of sensor used is not critical to the present disclosure and is shown only for completeness.

The stimulation device 10 additionally includes a battery 110 which provides operating power to all of the circuits shown in FIG. 3. The device 10 is shown in FIG. 3 as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (for example, up to 0.5 joules), moderate (for example, 0.5-10 joules), or high energy (for example, 11-40 joules), as controlled by the microcontroller 60. Such shocking pulses are applied to the patient's heart 12 through at least two shocking electrodes, and as shown in this embodiment, selected from the left atrial coil electrode 28, the right ventricular coil electrode 36, and the SVC coil electrode 38. As noted above, the housing 40 may act as an active electrode in combination with the right ventricular electrode 36, or as part of a split electrical vector using the SVC coil electrode 38 or the left atrial coil electrode 28 (i.e., using the right ventricular electrode 36 as a common electrode).

The device 10 includes two separate connection terminals, one for each of the two flexible conductors that are further connected to switch 74. The two flexible conductors can then be selectively connected as desired to the HIS sensing circuit 83, ventricular pulse generator 72, or impedance measuring circuit 112 for sensing, stimulating, and measuring tissue impedance at the site of the HIS bundle. Using the lead 21, it is possible to effect stimulation with the HIS tip electrode 16 and the HIS ring electrode 19, and to effect sensing with the conductive surfaces. According to another design, the sensing is affected by the conductive surfaces and stimulation is effected by means of the leads other than the HIS lead, for example the right atrial lead 20. For more details regarding a heart electrode equipped with multiple conductive surfaces, reference is made to U.S. Pat. Nos. 5,306,292 and 5,645,580, which are incorporated herein by reference. The HIS tip electrode 16 may be secured in the HIS bundle thereby anchoring the HIS tip electrode 16 in contact with the HIS bundle tissue. The electrogram signal arising from the HIS bundle can then be received by the HIS sensing circuit 83. A bypass filter (not shown) that allows signals ranging from 30-200 Hz to be received may be used to block the high frequency alternating current excitation signals.

Figure 4:
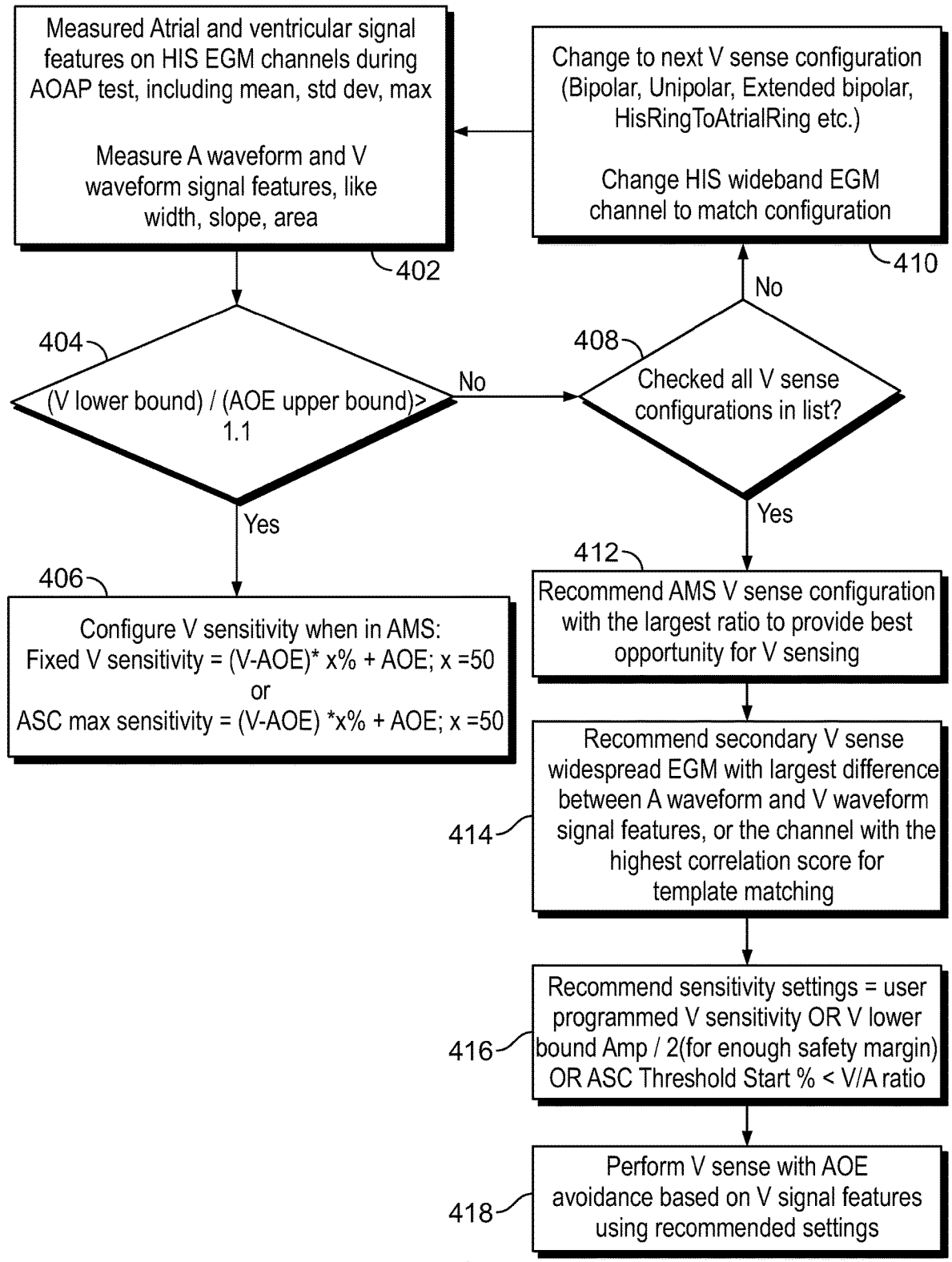
FIG. 4 illustrates a process for determining primary and secondary sensing configurations and sensitivity settings in accordance with embodiments herein.

Methods to Select, Validate and Utilize Sensing Configurations and Sensitivity Settings FIG. 4 illustrates a process for determining primary and secondary sensing configurations and sensitivity settings in accordance with embodiments herein. The process of FIG. 4 may be implemented in whole or in part by one or more processors within an IMD, a local external device and/or a remote server. The process of FIG. 4 leverages the processes described in the '698 provisional application, regarding atrial activity over sensing avoidance, by iteratively stepping through multiple primary sense configurations (e.g. in connection with a narrowband HIS sensing channel) and multiple secondary sensing configurations (e.g. in connection with a wideband HIS channel) and collecting CA signals for corresponding series of beats. The process of FIG. 4 identifies features of interest from the series of beats and compares relations between the features of interest to determine a recommendation regarding a select (e.g. preferred, optimal) primary sense configuration that meets certain V/A criteria, such as the V/A amplitude ratio criteria. Optionally, the process may further determine a select (e.g. preferred, optimal) secondary sense configuration, such as to maximize/optimize feature differentiation between A and V events. Additionally, the process determines candidate and resultant sensitivity settings to be utilized in connection with the resultant sensing configurations. By way of example, the sensitivity settings may include one or more of the parameters described in U.S. patent application Ser. No. 15/973,351, titled "METHOD AND SYSTEM TO DETECT R WAVES IN CARDIAC ARRHYTHMIC PATTERNS", filed May 7, 2018, the complete subject matter of which is expressly incorporated herein by reference in its entirety.

At 402, one or more processors collect CA signals utilizing candidate primary and secondary sensing configurations that are defined at least in part by a HIS sensing configuration that includes a HIS sensing vector that utilizes at least one HIS electrode located proximate to the HIS bundle and that is defined by a sensing channel that utilizes sensing circuitry configured to operate based on one or more sensing settings to detect near field and far field activity. The CA signals are collected over primary and secondary sensing channels. In accordance with some embodiments, the primary and secondary sensing channels may receive CA signals over a common sensing vector, namely a HIS sensing vector. Optionally, in accordance with other embodiments, the primary sensing channel receives CA signals collected over the HIS sensing vector, while the secondary sensing channel receives CA signals collected over a non-HIS sensing vector (e.g. a right atrial sensing vector that is defined between one or more right atrial electrodes).

All or a portion of the CA signals may be collected over a series of beats for the entire cardiac cycle within each beat (e.g. including the entire PQRST complex). Additionally or alternatively, all or a portion of the CA signals, collected over the series of beats, may be collected only for a select segment of each beat, such as during a predetermined window following a corresponding atrial sensed or paced event. For example, the predetermined window may correspond to the AOA window that is utilized in connection with the AOA processes described in the '698 provisional application. For example, the CA signals may be collected during the AOA window that is timed to follow atrial sensed events while the patient is experiencing intrinsic normal sinus rhythm, or to follow atrial paced events while a patient is experiencing a pacer assisted normal sinus rhythm.

The candidate HIS sensing configuration may utilize a HIS sensing vector that extends between a HIS ring electrode and an atrial ring electrode. Other examples of HIS sensing vectors are explained herein. The CA signals collected along the candidate HIS sensing vector are passed through sensing circuitry that defines one or more sensing channels, such as at least a primary sensing channel and optionally the secondary sensing channel. As a further option, the secondary sensing channel may receive CA signals collected along an RA sensing vector, such as the tip and ring RA electrodes. For example, the primary sensing channel may have settings that define a narrow passband, while the secondary sensing channel may have settings that define a wide passband.

The CA signals are collected over the primary and secondary sensing channels, in connection with the candidate sensing configuration(s), for a series of beats (e.g 5-30 beats, 5-30 seconds). Nonlimiting examples of the sensing settings for one or more parameters include gain, bandwidth, cutoff frequencies and the like. In the foregoing example, the one or more processors collect two data streams of CA signals, namely one data stream of CA signals passing through a narrowband/primary sensing channel (e.g. associated with a HIS sensing vector) and one stream of CA signals passing through a wideband/secondary sensing channel (e.g. associated with an RA sensing vector).

At 402, the one or more processors analyze the CA signals, collected over one or both of the primary and secondary sensing channels, to identify atrial (A) and ventricular (V) features of interest (FOI) for the corresponding beats within the series of beats. The same or different atrial and ventricular FOIs may be determined in connection with the narrowband/primary sensing channel and the wideband/secondary sensing channel. The atrial FOI may correspond to one or more features of an atrial over sensed event (AOE), various features of an atrial sensed event (P wave) and/or an atrial paced event.

For example, for each beat, the one or more processors may analyze the CA signals collected over the narrowband/primary sensing channel to identify an atrial over sensing event (AOE) that occurred during the AOA window and was detected over the HIS sensing channel/vector. The one or more processors further analyze the CA signals collected over the narrowband/primary sensing channel for a ventricular FOI that occurred during or after the AOA window.

For example, the one or more processors may identify a peak of the AOE as the atrial FOI, and a peak of the ventricular event as the ventricular FOI. The one or more processors identify the AOE peak and ventricular event peak for each beat, and from there determine the maximum AOE peak and maximum ventricular event peak. The one or more processors may further determine a mean amplitude, standard deviation and other mathematical relations between the AOE peaks and ventricular event peaks. A V-A FOI relation is subsequently determined, such as a ratio of the maximum peak of the AOE and the ventricular event, as well as a ratio of the mean amplitudes and standard deviations.

Optionally, other features of the AOE and/or ventricular event may be identified as the atrial and ventricular FOI from the narrowband/primary sensing channel during the AOA window and from the wideband/secondary sensing channel during the AOA window.

Additionally or alternatively, additional atrial and ventricular FOIs may be determined from the CA signals collected over the narrowband/primary sensing channel and/or the wideband/secondary sensing channel. For example, for each beat, the one or more processors may analyze the CA signals collected over the wideband/secondary sensing channel to identify an atrial event (AE) waveform segment. The AE waveform segment may be collected during the AOA window. Alternatively, the AOA window may not be utilized in connection with collecting the AE waveform segment. Instead, the AE waveform segment may correspond to an atrial paced or sensed event, that is utilized to define the start of the AOA window (e.g. in connection with identifying AOE atrial features of interest.

The one or more processors analyze the AE waveform segment for one or more atrial FOIs, such as a peak of the AE waveform segment, a width of the AE waveform segment, maximum slope, area under the curve and the like. As nonlimiting examples, the atrial FOI may be collected for a series of beats and combined utilizing a mathematical function, such as a mean, standard deviation and/or maximum value of the AE waveform segment with, maximum slope, area under the curve and the like.

Additionally, the one or more processors analyze the CA signals collected over the wideband/secondary sensing channel to identify, for each beat, a ventricular event (VE) waveform segment. The one or more processors analyze the VE waveform segment for one or more ventricular FOIs, such as a peak of the VE waveform segment, a width of the VE waveform segment, maximum slope, area under the curve and the like. As nonlimiting examples, the ventricular FOI may be collected for a series of beats and combined utilizing a mathematical function, such as a mean, standard deviation and/or maximum value of the VE waveform segment with, maximum slope, area under the curve and the like.

Additionally or alternatively, the VE waveform segment may be utilized to generate a ventricular template for a VE waveform that is captured during the AOA window. For example, the VE waveforms collected over a series of beats during the AOA window may be mathematically combined in various manners to form a V template At 404, the one or more processors further identify a V-A FOI relation between the A FOIs and the V FOIs across the series of beats. The one or more processors determine an A boundary for the A FOIs over the series of beats and a V boundary for the V FOIs over the series of beats. For example, the one or more processors may determine a lower boundary of the ventricular FOI and an upper boundary of the atrial FOI for the series of beats. The lower boundary may represent a lowest value of the ventricular FOI collected over the series of beats. The upper boundary of the atrial FOI may represent an upper/highest value of the atrial FOI collected over the series of beats. The one or more processors determine whether the ratio of the lower boundary of the ventricular FOI and the upper boundary of the atrial FOI exceed a predetermined threshold (e.g. a value greater than one).

Additionally or alternatively, the analysis at 404 may identify an V-A FOI relation between the mean of the atrial FOI and the mean of the ventricular FOI. Additionally or alternatively, the V-AV FOI relation may include a mean plus standard deviation relation between the atrial and ventricular features of interest. Additionally or alternatively, the A-V FOI relation may include a maximum of the atrial feature of interest to be compared to the mean of the ventricular feature of interest. Additionally or alternatively, V-A FOI relation may include the standard deviation of the ventricular amplitude lower boundary that is mathematically combined (e.g. divided by) with the standard deviation of the atrial amplitude standard deviation upper limit. The boundaries can be defined in various manners, such as by a range or other mechanism, such as confidence intervals or percentage from the median and the like.

When the ratio exceeds the threshold, flow moves to 406. When the ratio does not exceed the threshold, flow moves to 408. Optionally, the one or more processors may also determine an upper boundary of the ventricular FOI and a lower boundary of the atrial FOI and analyze such boundaries with respect to one or more corresponding thresholds.

At 406, the one or more processors configure the ventricular sensitivity profile to be utilized in connection with a non-tracking mode. For example, the ventricular sensitivity profile may be set to a fixed value based on the atrial FOI. For example, the ventricular sensitivity profile may be set as is a straight line sensitivity level: $V_{SENS}=(V-ACE)*x \%+AOE$, where V corresponds to the upper boundary of the ventricular FOI from the series of beats, x % represents a desired percentage (e.g. 50%), and the AOE represents a mathematical combination of the atrial FOIs over the series of beats (e.g. mean of the amplitude of an atrial over sensing event).

Additionally or alternatively, the one or more processors may set the automatic sensing control (ASC) maximum sensitivity to a fixed value based on the atrial FOI (e.g. the AOE). For example, the ASC maximum sensitivity may be set as: $ASC_{MAX}=(V-AOE)*x \%+AOE$, where V corresponds to the upper boundary of the ventricular FOI from the series of beats, x % represents a desired percentage (e.g. 50%), and the AOE represents a mathematical combination of the AOEs over the series of beats (e.g. mean of the amplitude of an atrial over sensing event). Additionally or alternatively, the ASC maximum sensitivity may be set based on a different formula defining a function between the ventricular FOI and the atrial FOI.

At 408, the one or more processors determine whether all primary sensing configurations have been analyzed at 402-404. For example, a list of primary sensing configurations may be maintained, where the list includes sets of parameters associated with each sensing configuration. At 408, the one or more processors determine whether the various sets of parameters have been utilized at 402, 404. Additionally or alternatively, the determination at 408 may step through a series of increments in one or more parameters.

Nonlimiting examples of sensing configurations include a bipolar sensing configuration, a unipolar sensing configuration, an extended bipolar sensing configuration, as well as various sensing vectors defined by corresponding combinations of sensing electrodes. For example, a first sensing vector may extend between a HIS ring electrode and an atrial ring electrode, while a second sensing vector may extend between a HIS tip electrode and the atrial ring electrode, while a third sensing vector may extend between the HIS ring electrode and an atrial tip electrode. Additionally or alternatively, the sensing vector may extend between a HIS ring and/or tip electrode and one or more RV electrodes and/or one or more LV electrodes. Additional sensing configurations include His bipolar (His tip to ring), His unipolar (His tip to Can, His Ring to Can), and extended bipolar (His Tip or His Ring to any electrodes on the other available pacing leads such as A, RV, or LV). Each combination of electrodes, as used to define a corresponding sensing vector, may be similarly switched between bipolar, unipolar and extended bipolar configurations.

Additionally or alternatively, at 408, the one or more processors may change the HIS sensing channel to match the current sensing configuration. If not all candidate sensing configurations have been analyzed, the device would automatically use the next untested sensing configuration as the His sensing channel and rerun the analysis (402). Thereafter flow returns to 402. The operations at 402-410 are iteratively repeated until the ratio of the lower boundary of the ventricular FOI and upper boundary of the atrial FOI satisfy the threshold test at 404 or until all HIS and/or RA sensing configurations have been tested.

Figure 5A:
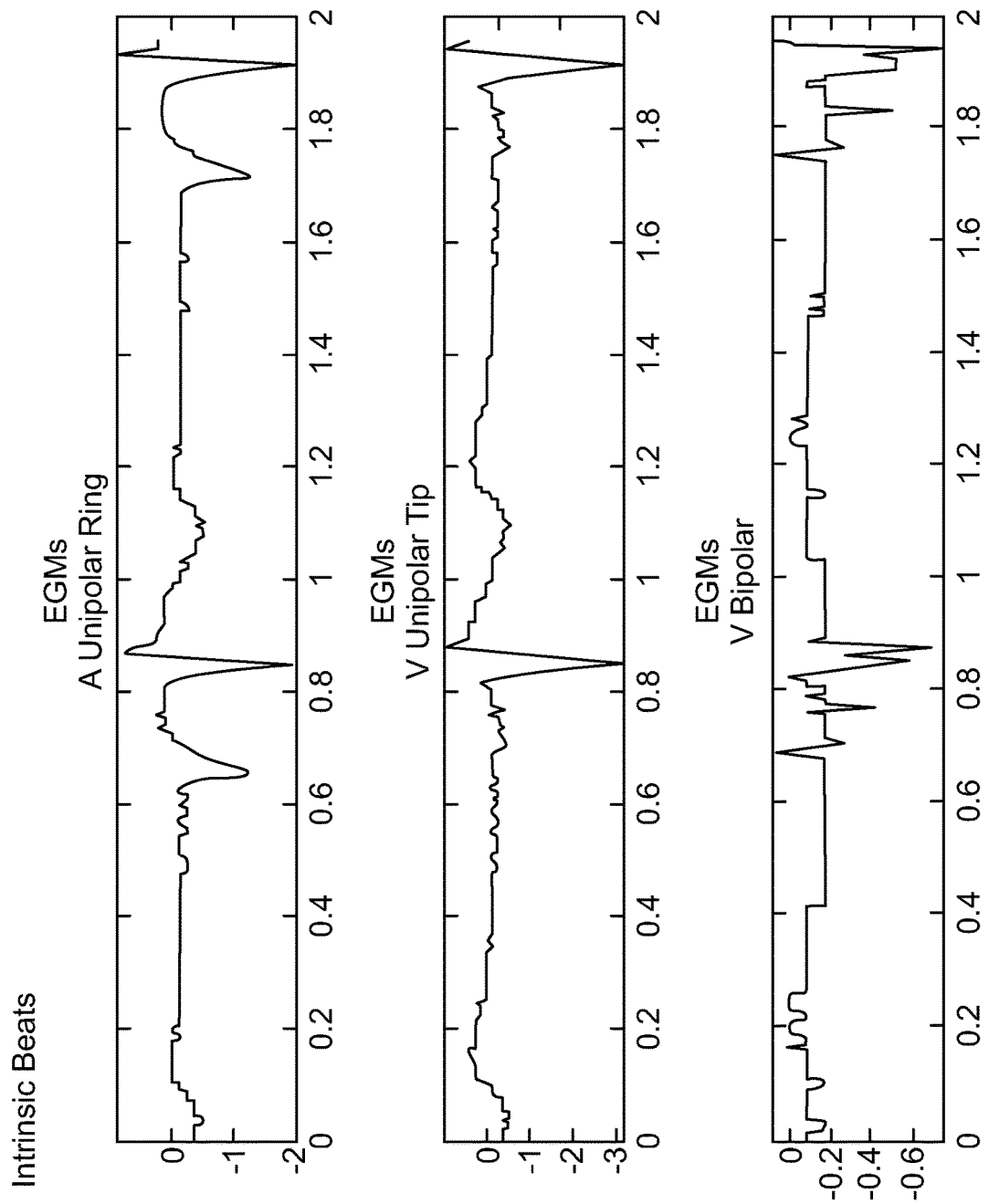
FIGS. 5A and 5B illustrate examples of CA signals collected over different sensing channels utilizing different sensing configurations in accordance with embodiments herein.
Figure 5B:
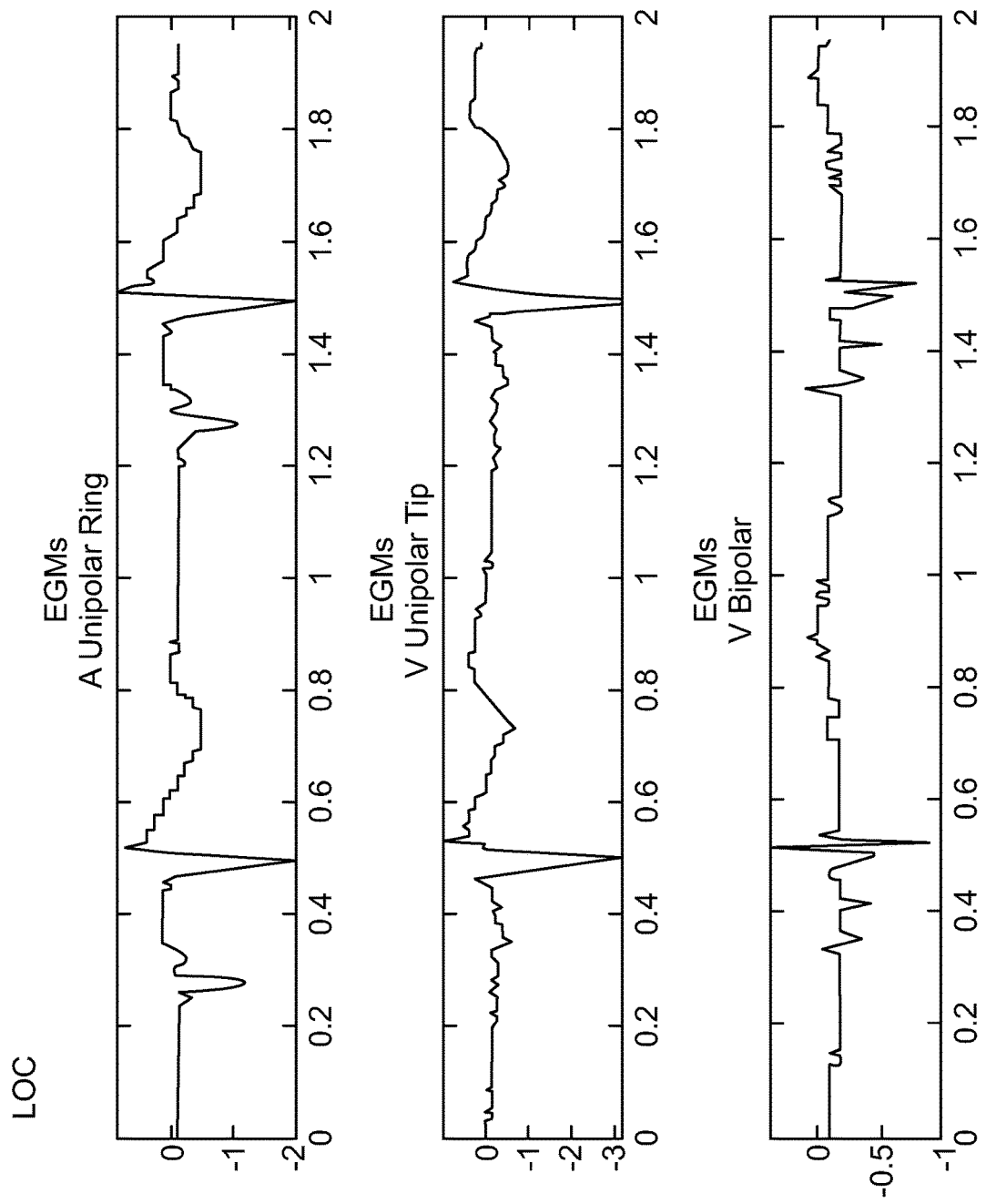

FIGS. 5A and 5B illustrate examples of CA signals collected over different sensing channels utilizing different sensing configurations in accordance with embodiments herein. The three leftmost panels in FIG. 5A correspond to intrinsic beats, while the three rightmost panels in FIG. 5B correspond to HIS bundle paced beats where the pacing pulse resulted in loss of capture (LOC).

The upper left CA signal trace corresponds to a RA sensing vector utilizing right atrial ring electrode in a unipolar configuration. The middle left CA signal trace corresponds to a HIS sensing vector utilizing a tip electrode located proximate the HIS bundle in the RV and arranged in a unipolar sensing configuration. The bottom left CA signal trace corresponds to a HIS sensing vector utilizing HIS electrodes arranged in a bipolar sensing configuration.

The upper right CA signal trace corresponds to a RA sensing vector utilizing right atrial ring electrode in a unipolar configuration. The middle right CA signal trace corresponds to a HIS sensing vector utilizing a tip electrode located proximate to the HIS bundle in the RV and arranged in a unipolar sensing configuration. The bottom right CA signal trace corresponds to a HIS sensing vector utilizing HIS electrodes arranged in a bipolar sensing configuration.

As shown in FIG. 5, the ventricular QRS complex, as measured over a HIS sensing vector/channel aligns well with the ventricular QRS complex, as measured over an RA sensing vector/channel while in sinus rhythm. The ventricular peak locations align as measured over the HIS and RA sensing vectors/channels in unipolar and bipolar configurations.

Returning to the process of FIG. 4, embodiments herein extract a feature of interest (e.g. ventricular peak amplitude) in connection with the current/candidate HIS configuration and a ventricular feature is assessed relative to an atrial feature, such as the atrial amplitude. The comparison seeks to limit/minimize the complexity of the analysis. When the ventricular signal is larger than the atrial signal for any given HIS configuration, the corresponding configuration is determined to be able to sense ventricular signals reliably during an atrial arrhythmia such as AT or AF by configuring a sensitivity to be larger than the normal atrial channel sensitivity utilized to identify atrial events. Each and every potential configuration need not be considered, but instead the process moves from 404 to 406 when anyone of the candidate sensing configurations satisfies the corresponding criteria.

Returning to 408, when all sensing configurations have been tested, flow moves to 412.

At 412, the one or more processors determine a resultant HIS sensing configuration to be utilized during the non-tracking mode. For example, the resultant HIS/primary sensing configuration may be the configuration that exhibits the largest ratio between the ventricular FOI lower boundary and atrial FOI upper boundary, in order to provide a best opportunity to sense ventricular events over the HIS sensing vector.

At 414, the one or more processors determine a resultant secondary sensing configuration for the wideband sensing channel. As noted above, the wideband/secondary sensing configuration may be configured to sense EGM signals over a HIS sensing vector or an RA sensing vector. The resultant secondary sensing configuration may be designated as the configuration that yields the largest difference between one or more features of interest from the AE waveform and one or more features of interest from the VE waveform. Additionally or alternatively, the configuration for the wideband channel may be selected as the configuration that yields the highest correlation score when the VE waveform is correlated to one or more ventricular templates. As noted herein, the A FOI may represent an AOE FOI. For example, the one or more processors may quantify a difference in each FOI by comparing the FOIs derived from the AOE versus features derived from the ventricular signal. The one or more processors may select the settings for the wideband channel that have a largest difference between the AOE signal features and the ventricular signal features. As one example, the difference in features may be quantified as a probability score using a maximum slope, area and/or amplitude of the AOE signal features versus the maximum slope, area and/or amplitude of the corresponding ventricular signal feature.

Additionally or alternatively, the resultant HIS sensing configuration and/or the resultant secondary sensing configuration may be determined in whole or in part based on a correlation score for correlation between one or more templates and a corresponding FOI. For example, the correlation score may be derived, in connection with each candidate HIS sensing vector, where the score indicates a degree of correlation between the VE waveform and a ventricular template. The HIS sensing configuration that yields the best correlation between the VE waveform and ventricular template may be designated as the resultant HIS sensing configuration.

Nonlimiting examples of correlation techniques include algorithms that utilize Pearson's coefficient, Kendall's rank, Kendall Tau template scores, Spearman's rank, triangular morphology matching and the like.

At 416, the one or more processors determine a resultant sensitivity setting to be used with one or both of the primary and secondary sensing configurations. For example, the resultant sensitivity setting may correspond to a programmed sensitivity for the HIS/primary sensing channel. Alternatively, the sensitivity setting may be set as a function of the lower boundary of the amplitude of the ventricular FOI (e.g. equal to the ventricular amplitude lower boundary divided by two). The sensitivity setting may be adjusted to include a desired safety margin. Optionally, the ASC threshold start point may be set to correspond to a percentage of the V/A amplitude ratio.

At 418, the one or more processors utilize the resulted HIS/primary sensing configuration and secondary sensing configuration to manage HIS bundle pacing during an atrial arrhythmia.

Next, the discussion turns to methods and systems to assess the A and V FOI determined in connection with the primary and secondary sensing configurations. For example, an in-clinic sense test may be performed while a patient is experiencing sinus rhythm, where the test is applied in connection with an AOA process. The AOA process identifies V sensed events which are then used as benchmarks/standards for comparison with feature classification of these sensed events that are determined utilizing the resultant HIS and secondary sensing configurations determined in connection with FIG. 4. The comparison determines a performance of the sensed event classified using the configuration determined in connection with FIG. 4 and will determine whether the identified features reliably identify the V sensed events.

Figure 6:
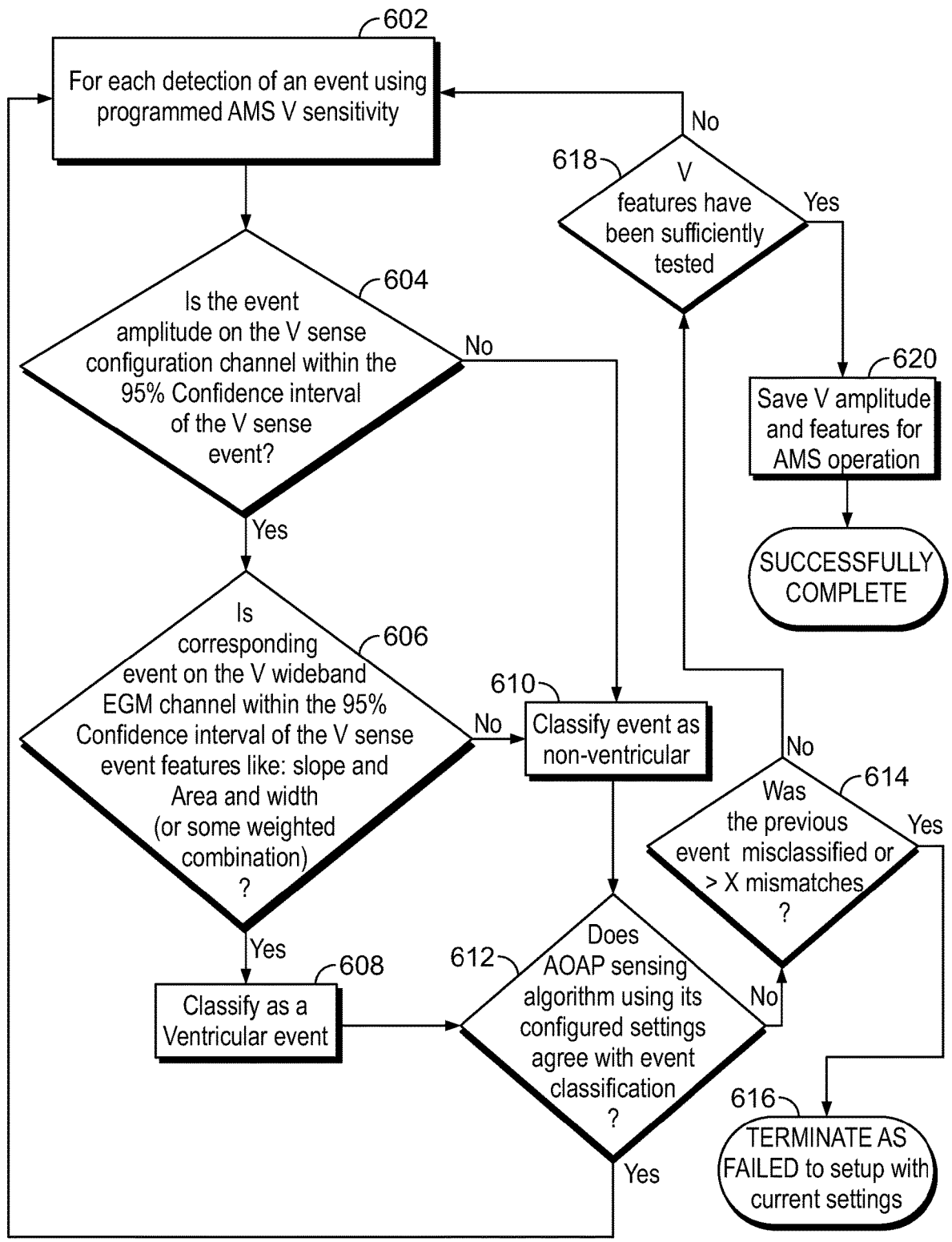
FIG. 6 illustrates a process for validating the resultant sensing configurations and sensitivities determined in connection with the process of FIG. 4.

FIG. 6 illustrates a process for validating the resultant sensing configurations and sensitivities determined in connection with the process of FIG. 4. The process of FIG. 6 seeks to validate the resultant sensing configurations and sensitivities concurrently with a process for determining atrial over sensing avoidance parameters and settings, such as described in the '698 provisional application. The processes described in the '698 provisional application provide reference AOA parameters and settings. In parallel therewith, the process of FIG. 6 monitors a patient's cardiac activity by collecting new CA signals utilizing the resultant primary and secondary sensing configurations. The process of FIG. 6 further analyzes the incoming CA signals utilizing the resultant sensitivity set at 416 to identify candidate ventricular events.

In accordance with new and unique aspects herein, it is expected that the ventricular peak amplitude will remain stable during an atrial arrhythmia (AF or AT). The calibration process of FIG. 4 provides baseline amplitudes for ventricular and atrial events during sinus rhythms. In accordance with aspects herein, a confidence interval of ventricular amplitudes is defined based on the baseline amplitudes for the ventricular and atrial events. The confidence interval represents a V peak zone or range of acceptable ventricular amplitudes. For example, the zone or range can be defined to correspond to a mean ventricular amplitude plus/minus $\alpha*SD$, where SD corresponds to the standard deviation of the ventricular amplitude and a can be set to 1, 1.5, 2, etc. based on a desired percentage of confidence interval. During an atrial arrhythmia (AF/AT), if a sensed ventricular peak falls outside of the V peak zone, the event is considered a non-ventricular beat and is excluded from subsequent analysis/counting. Alternatively, if a sensed ventricular beat falls inside of the V peak zone, the process to analyze features of interest from the ventricular event (e.g. with, maximum slope, area, morphology, etc.), and based thereon classifies the event as a ventricular sensed event or a non-ventricular sensed event. The classified event of (e.g. ventricular or non-ventricular) result is compared to the result from the AOA process for the same beat. As explained in the 698 provisional application, the AOA process classify an event, as a non-ventricular event, when the event occurs during the AOA window at an amplitude lower than a prescribed AO sensitivity. Alternatively, the AOA process for classify the event as a ventricular event, when the event occurs during the AOA window at an amplitude that exceeds the prescribed AOA sensitivity.

When event classifications match for the AOA process and the process of FIG. 6, a counter is incremented indicating a successful test of the feature-based ventricular sensing classifier, when utilizing the resultant sensing configurations and sensitivities as set in FIG. 4. When a sufficient number of events match between the present feature-based ventricular sensing classifier and the AOA process, the resultant sensing configuration and sensitivity are confirmed/verified and subsequently used during normal operation of the IMD. Alternatively, if the present feature-based ventricular sensing classifier and the AOA process disagree for consecutive beats or a set number of beats out of a collection of beats (e.g. three out of 10 beats), the resultant sensing configurations and sensitivity may be denied or otherwise declared unacceptable. In response thereto, the process of FIG. 4 may be repeated or other adjustments may be applied.

At 602, the IMD is set to operate in a non-tracking mode and begins collecting CA signals over the HIS sensing channel, while utilizing the resultant sensing configurations and sensitivities determined in connection with FIG. 4. At 602, the one or more processors compare the incoming CA signals to a ventricular sensitivity and declare candidate ventricular events when the CA signals exceed the ventricular sensitivity threshold.

At 604, the one or more processors determine whether an amplitude of the event identified over the HIS sensing channel is within a confidence interval for expected the sensed events. For example, the confidence interval may be defined as a percentage (e.g. 95% confidence interval). The confidence interval may be preprogrammed or may be defined based on the ventricular FOIs identified in connection with FIG. 4, such as based on the mean and standard deviation determined from the VE waveform segments measured at 402. When the amplitude of the event is within the confidence interval, flow moves to 606. When the amplitude of the event is not within the conference interval, flow moves to 610.

At 610, the one or more processors classify the event as non-ventricular. Thereafter, flow moves to 612.

At 606, the one or more processors analyze the CA signals collected over the secondary sensing channel (e.g. the RA sensing channel) to determine whether a corresponding event occurred. At 606, the one or more processors further determine whether the candidate event, collected over the secondary sensing channel, exhibits a ventricular FOI that falls within a confidence interval. For example, the candidate event may be analyzed to determine whether a slope, area, with, combination thereof, weighted combination thereof or otherwise fall within a 95% confidence interval. The 95% confidence interval may be preprogrammed or defined based on the corresponding features from the ventricular event waveforms identified by the process of FIG. 4.

When the corresponding event over the secondary sensing channel exhibits one or more features of interest that are within the confidence interval, flow moves to 608. When the corresponding event exhibits one or more features of interest that are not within the confidence interval, flow moves to 612.

At 608, the one or more processors classify the event as a ventricular event. Thereafter, flow moves to 612.

At 612, the one or more processors determine whether the classification at 610 or 608 matches a classification independently determined by the AOA algorithm. When the process at 602-610 results in a common output as the AOA algorithm, flow returns to 602. When the process at 602-610 results in a different output than the AOA algorithm, flow moves to 614.

At 614, it is determined whether the previous event was misclassified. For example, the determination of misclassification may be determined manually by a physician or automatically through additional signal analysis by the one or more processors. Additionally or alternatively, it may be determined whether the number of mismatches (between the operations at 602-610 versus the AOA algorithm) has exceeded a threshold. Based on the germination 614, flow branches to 616 or 618.

At 616, the process terminates in the system determines that there is a failure to set up the IMD with current settings. At 618, the one or more processors determine whether a sufficient number of ventricular events have been tested. When more ventricular events are to be tested, flow returns to 602. When a sufficient number of ventricular events of been tested, flow moves to 620. At 620, the one or processors save the A FOIs and V FOIs, including but not limited to the ventricular amplitude, for use during a non-tracking mode of operation. Thereafter, the confirmation process of FIG. 6 is completed.

Next, the discussion moved to the operation of the IMD during normal use.

Figure 7:
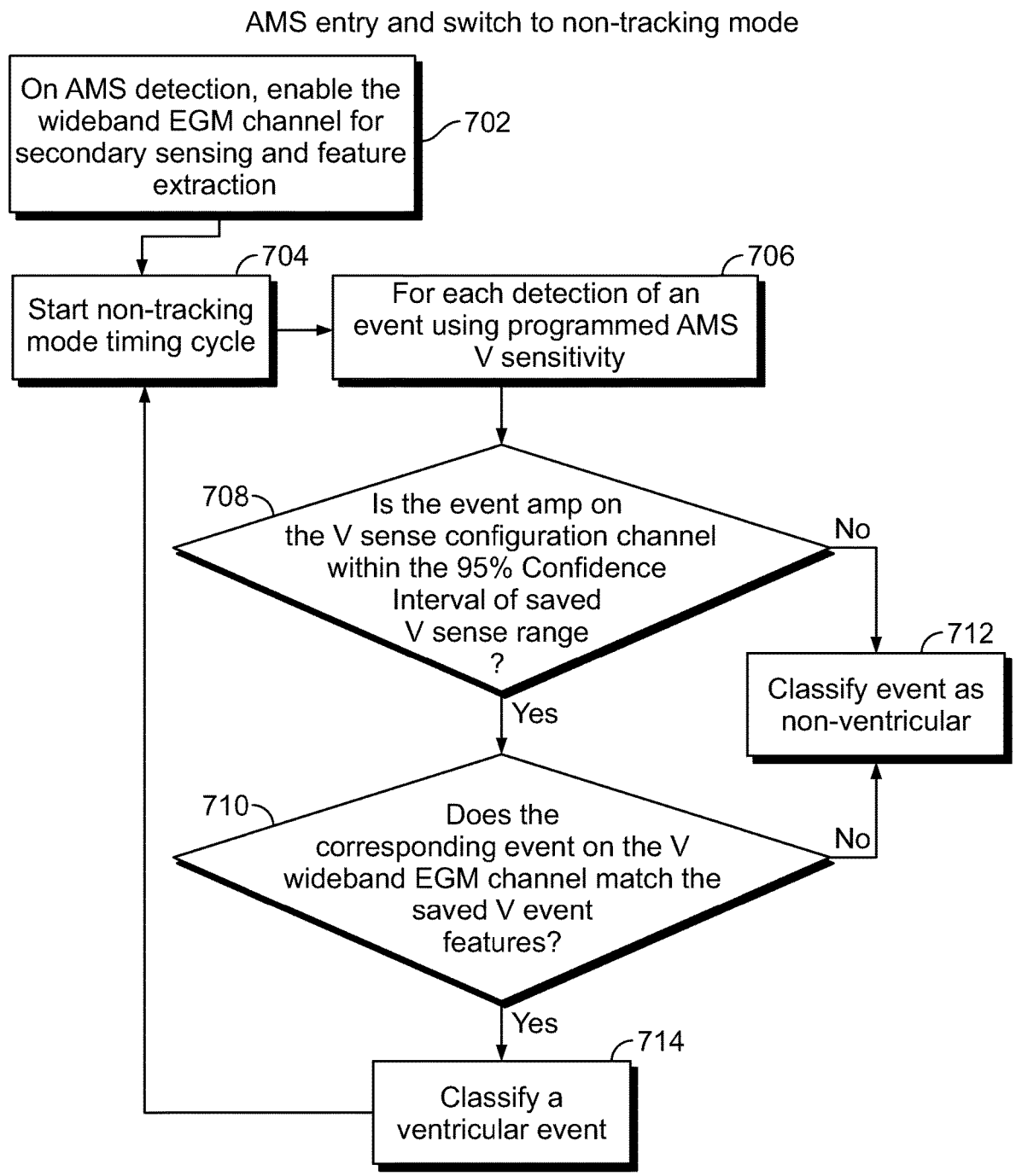
FIG. 7 illustrates a process by which the IMD manages HIS bundle pacing when entering automatic mode switching to a non-tracking mode in accordance with embodiments herein.

FIG. 7 illustrates a process by which the IMD manages HIS bundle pacing when entering automatic mode switching to a non-tracking mode in accordance with embodiments herein. At 702, the one or more processors detect an AMS condition. At 702, the one or more processors enable the wideband channel for secondary sensing and feature analysis based on the secondary sensing configuration and sensitivity profile identified in connection with FIG. 4.

At 704, the one or more processors begin a non-tracking mode timing cycle. At 706, the one or more processors monitors the incoming CA signals over the wideband/secondary sensing channel utilizing a non-tracking mode ventricular sensitivity that has been previously programmed or automatically determined in order to detect ventricular events. When a candidate ventricular event is detected 706 over the wideband/secondary sensing channel, flow moves to 708.

At 708, the one or more processors analyzes the CA signals collected over the HIS/primary sensing channel to identify a corresponding event matching the candidate ventricular event was detected over the wideband/secondary sensing channel. At 708, the one or more processors extract a ventricular feature of interest from the CA signals collected over the HIS/primary sensing channel and determine whether the ventricular FOI (e.g. ventricular amplitude) falls within a confidence interval of a saved ventricular FOI (e.g. ventricular sense range). When the V FOI falls within the confidence interval, flow moves to 710. When the V FOI does not fall within the confidence interval, flow moves to 712. At 712, the one or processors classify the candidate event as a non-ventricular event.

At 710, the one or more processors determine whether the corresponding event on the wideband/secondary channel exhibits an FOI that matches a saved ventricular FOI. When a match does not occur, flow moves to 712, where the candidate event is classified as a non-ventricular event. Alternatively, when a match does occur, flow moves to 714 where the candidate event is classified as a ventricular event. Following the classification said 14, flow returns to 704 where the non-tracking mode is continued.

External Device

Figure 8:
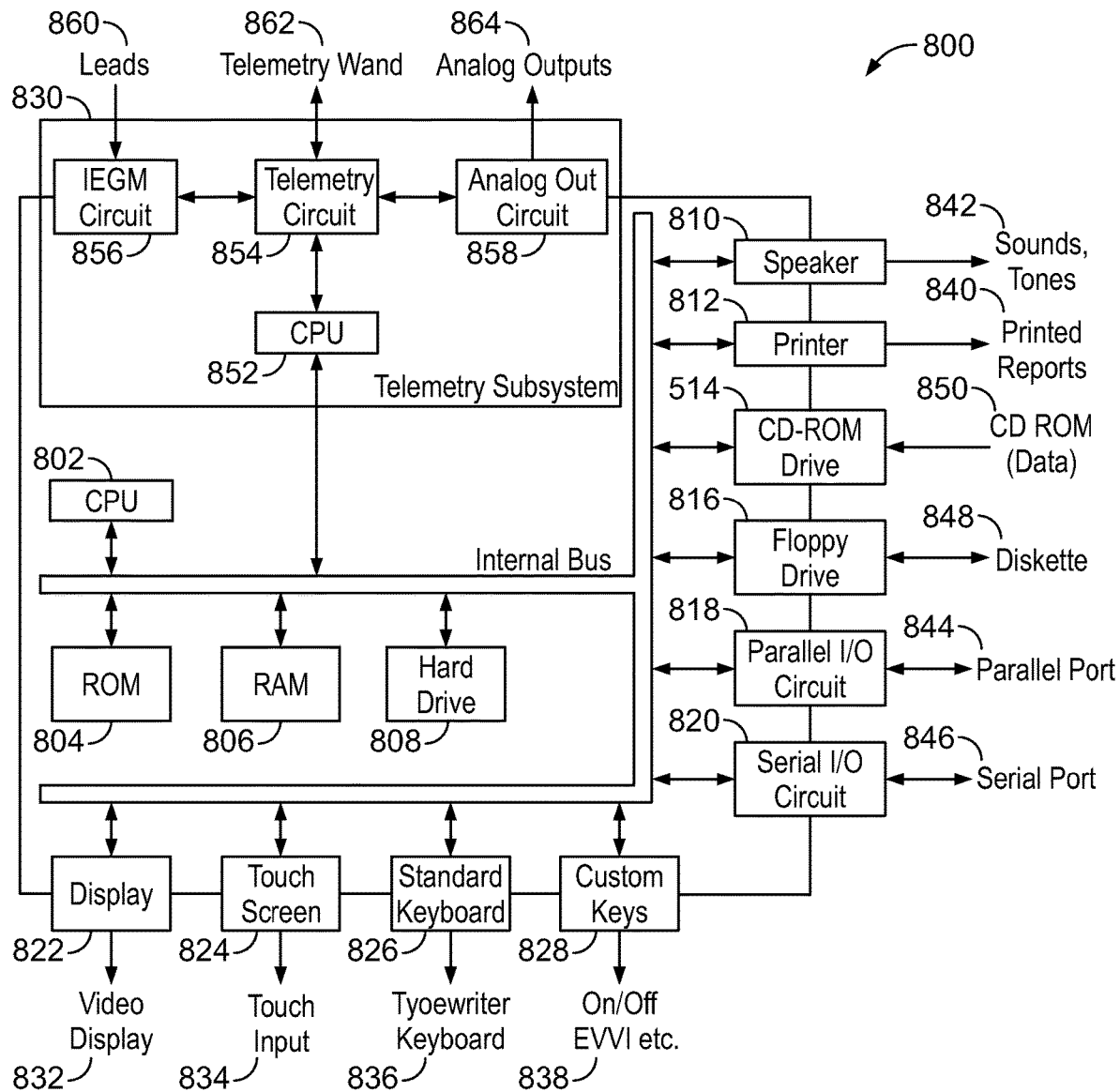

FIG. 8 illustrates a functional block diagram of the external device 800 that is operated in accordance with the processes described herein and to interface with implantable medical devices as described herein. The external device 800 may be a workstation, a portable computer, an IMD programmer, a PDA, a cell phone and the like. The external device 800 includes an internal bus that connects/interfaces with a Central Processing Unit (CPU) 802, ROM 804, RAM 806, a hard drive 808, the speaker 810, a printer 812, a CD-ROM drive 814, a floppy drive 816, a parallel I/O circuit 818, a serial I/O circuit 820, the display 822, a touch screen 824, a standard keyboard connection 826, custom keys 828, and a telemetry subsystem 830. The internal bus is an address/data bus that transfers information between the various components described herein. The hard drive 808 may store operational programs as well as data, such as waveform templates and detection thresholds.

The CPU 802 typically includes a microprocessor, a micro-controller, or equivalent control circuitry, designed specifically to control interfacing with the external device 800 and with the IMD 100. The CPU 802 performs the process discussed above. The CPU 802, when executing the program instructions, is configured to implement a HIS configuration manager that, among other things, analyze the CA signals to obtain an atrial (A) feature of interest (FOI) and a ventricular (V) FOI for the corresponding beats within the series of beats; identify a V-A FOI relation between the A FOIs and the V FOIs across the series of beats; adjust the candidate sensing configuration and repeat the obtain, analyze and identify operations to obtain a collection of V-A FOI relations for a corresponding collect of candidate sensing configurations; select a resultant sensing configuration from the collection of candidate sensing configurations based on one or more criteria, the resultant sensing configuration to be utilized to manage HIS bundle pacing during an atrial arrhythmia.

The HIS configuration manager is further configured to determine an A boundary for the A FOIs over the series of beats and a V boundary for the V FOIs over the series of beats. Additionally or alternatively, the HIS configuration manager is further configured to determine a lowest value of the V FOIs collected over the series of beats, and an upper value of the A FOIs collected over the series of beats, the identify operation further comprising determining whether a ratio of the lower value of the V FOIs and the upper value of the A FOIs exceed a predetermined threshold. Additionally or alternatively, the HIS configuration manager is further configured to identify the V-A FOI relation by calculating a relation between at least one of means, means plus standard deviations, amplitudes or standard deviations between the V FOI and the A FOI. Additionally or alternatively, the HIS configuration manager is further configured to determine a ventricular sensitivity based on the resultant sense configuration; and to configure the implantable medical device to, during a non-tracking mode, utilize the ventricular sensitivity to detect ventricular events from the CA signals collected over the HIS sensing vector and a HIS sensing channel, wherein the implantable medical device does not time HIS bundle pacing based on atrial paced or sensed events during the non-tracking mode. Additionally or alternatively, the HIS configuration manager is further configured to implement a verification process to verify the resultant HIS sensing configuration in parallel with an atrial oversensing avoidance (AOA) process.

The CPU 802 may include RAM or ROM memory, logic and timing circuitry, state machine circuitry, and I/O circuitry to interface with the IMD 100. The display 822 (e.g., may be connected to the video display 832). The touch screen 824 may display graphic information relating to the IMD 100. The display 822 displays various information related to the processes described herein. The touch screen 824 accepts a user's touch input 834 when selections are made. The keyboard 826 (e.g., a typewriter keyboard 836)

allows the user to enter data to the displayed fields, as well as interface with the telemetry subsystem 830. Furthermore, custom keys 828 turn on/off 838 (e.g., EWI) the external device 800. The printer 812 prints copies of reports 840 for a physician to review or to be placed in a patient file, and speaker 810 provides an audible warning (e.g., sounds and tones 842) to the user. The parallel I/O circuit 818 interfaces with a parallel port 844. The serial I/O circuit 820 interfaces with a serial port 846. The floppy drive 816 accepts diskettes 848. Optionally, the floppy drive 816 may include a USB port or other interface capable of communicating with a USB device such as a memory stick. The CD-ROM drive 814 accepts CD ROMs 850.

The telemetry subsystem 830 includes a central processing unit (CPU) 852 in electrical communication with a telemetry circuit 854, which communicates with both an IEGM circuit 856 and an analog out circuit 858. The circuit 856 may be connected to leads 860. The circuit 856 is also connected to the implantable leads 114, 116 and 118 to receive and process IEGM cardiac signals as discussed above. Optionally, the IEGM cardiac signals sensed by the leads 114, 116 and 118 may be collected by the IMD 100 and then transmitted, to the external device 800, wirelessly to the telemetry subsystem 830 input.

The telemetry circuit 854 is connected to a telemetry wand 862. The analog out circuit 858 includes communication circuits to communicate with analog outputs 864. The external device 800 may wirelessly communicate with the IMD 100 and utilize protocols, such as Bluetooth, GSM, infrared wireless LANs, HIPERLAN, 3G, satellite, as well as circuit and packet data protocols, and the like. Alternatively, a hard-wired connection may be used to connect the external device 800 to the IMD 100.

CLOSING STATEMENTS

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

All references, including publications, patent applications and patents, cited herein are hereby incorporated by reference to the same extent as if each reference were individually and specifically indicated to be incorporated by reference and were set forth in its entirety herein.

What is claimed is:

1. A system, comprising:
   a HIS electrode configured to be located proximate to a HIS bundle and to at least partially define a HIS sensing vector;
   memory to store program instructions and cardiac activity (CA) signals for a series of beats utilizing a candidate sensing configuration, the candidate sensing configuration defined by i) the HIS sensing vector and ii) a sensing channel that utilizes sensing circuitry configured to operate based on one or more sensing settings to detect near field and far field activity;
   one or more processors that, when executing the program instructions, are configured to:
   analyze the CA signals to obtain an atrial (A) feature of interest (FOI) and a ventricular (V) FOI for corresponding beats within the series of beats;
   identify a V-A FOI relation between the A FOIs and the V FOIs across the series of beats;
   adjust the candidate sensing configuration between at least one of multiple HIS sensing vectors or multiple sensing settings, and repeat the obtain, analyze and identify operations to obtain a collection of V-A FOI relations for a corresponding collection of candidate sensing configurations; and
   select a resultant sensing configuration from the collection of candidate sensing configurations based on one or more criteria, the resultant sensing configuration to be utilized to manage HIS bundle pacing during an atrial arrhythmia.

2. The system of claim 1, wherein the one or more processors are further configured to determine an A boundary for the A FOIs over the series of beats and a V boundary for the V FOIs over the series of beats.

3. The system of claim 2, wherein the one or more processors are further configured to determine a lowest value of the V FOIs collected over the series of beats, and an upper value of the A FOIs collected over the series of beats, the identify operation further comprising determining whether a ratio of the lowest value of the V FOIs and the upper value of the A FOIs exceed a predetermined threshold.

4. The system of claim 1, wherein the one or more processors are further configured to identify the V-A FOI relation by calculating a relation between at least one of means, means plus standard deviations, amplitudes or standard deviations between the V FOI and the A FOI.

5. The system of claim 1, wherein the HIS electrode is configured to be located in one of a right atrium or right ventricle proximate to the HIS bundle.

6. The system of claim 1, further comprising an implantable medical device (IMD), the IMD including a header configured to be coupled to a lead having the HIS electrode located proximate to a distal end of the lead, the IMD including IMD memory and an IMD processor, the IMD memory configured to store the resultant sensing configuration, the IMD processor configured to utilize the resultant sensing configuration to manage the HIS bundle pacing during the atrial arrhythmia.

7. The system of claim 1, wherein the HIS sensing vector is defined by electrodes that includes the HIS electrode and at least one additional electrode, and wherein to adjust the candidate sensing configuration, the one or more processors are further configured to, at least one of:
   i) switch the HIS sensing vector between at least two of a bipolar configuration, a unipolar configuration or an extended bipolar configuration;
   ii) switch the HIS sensing vector between at least first and second combinations of the electrodes; or
   iii) switch the sensing channel between first and second sensing settings.

8. The system of claim 1, wherein the HIS sensing vector is defined by electrodes that includes the HIS electrode and at least one additional electrode, the HIS electrode including at least one of a HIS tip electrode or a HIS ring electrode, the at least one additional electrode including at least one of an atrial ring electrode, an atrial tip electrode, a CAN electrode, a right ventricular electrode or a left ventricular electrode, and wherein to adjust the candidate sensing configuration, the one or more processors are further configured to switch the HIS sensing vector between first and second combinations of the HIS electrode and the at least one additional electrode.

9. The system of claim 1, wherein the sensing circuitry is configured to operate based on first and second sensing parameter sets, and wherein to adjust the candidate sensing configuration, the one or more processors are further configured to switch between the first and second sensing parameter sets.

10. An implantable medical device (IMD), comprising:
a lead having a HIS electrode configured to be located proximate to a HIS bundle to at least partially define a HIS sensing vector;
memory to store program instructions;
sensing circuitry configured to define a sensing channel and to be coupled to the HIS electrode to collect cardiac activity (CA) signals for a series of beats utilizing a candidate sensing configuration, the candidate sensing configuration defined by i) the HIS sensing vector and ii) the sensing channel;
one or more processors that, when executing the program instructions, are configured to:
analyze the CA signals to obtain an atrial (A) feature of interest (FOI) and a ventricular (V) FOI for corresponding beats within the series of beats;
identify a V-A FOI relation between the A FOIs and the V FOIs across the series of beats;
adjust the candidate sensing configuration between at least one of multiple HIS sensing vectors or multiple sensing settings, and repeat the obtain, analyze and identify operations to obtain a collection of V-A FOI relations for a corresponding collection of candidate sensing configurations; and
select a resultant sensing configuration from the collection of candidate sensing configurations based on one or more criteria, the resultant sensing configuration to be utilized to manage HIS bundle pacing during an atrial arrhythmia.

11. The IMD of claim 10, wherein the one or more processors are further configured to determine an A boundary for the A FOIs over the series of beats and a V boundary for the V FOIs over the series of beats.

12. The IMD of claim 10, wherein the one or more processors are further configured to determine a lowest value of the V FOIs collected over the series of beats, and an upper value of the A FOIs collected over the series of beats, the identify operation further comprising determining whether a ratio of the lowest value of the V FOIs and the upper value of the A FOIs exceed a predetermined threshold.

13. The IMD of claim 10, wherein the one or more processors are further configured to identify the V-A FOI relation by calculating a relation between at least one of means, means plus standard deviations, amplitudes or standard deviations between the V FOI and the A FOI.

14. The IMD of claim 10, further comprising electrodes that include the HIS electrode and at least one additional electrode, and wherein to adjust the candidate sensing configuration, the one or more processors are further configured to, at least one of:
iv) switch the HIS sensing vector between at least two of a bipolar configuration, a unipolar configuration or an extended bipolar configuration;
v) switch the HIS sensing vector between at least first and second combinations of the electrodes; or
vi) switch the sensing channel between first and second sensing settings.

15. The IMD of claim 10, further comprising electrodes that include the HIS electrode and at least one additional electrode, the HIS electrode including at least one of a HIS tip electrode or a HIS ring electrode, the at least one additional electrode including at least one of an atrial ring electrode, an atrial tip electrode, a CAN electrode, a right ventricular electrode or a left ventricular electrode, and wherein to adjust the candidate sensing configuration, the one or more processors are further configured to switch the HIS sensing vector between first and second combinations of the HIS electrode and the at least one additional electrode.

16. The IMD of claim 10, wherein the sensing circuitry is configured to operate based on first and second sensing parameter sets, and wherein to adjust the candidate sensing configuration, the one or more processors are further configured to switch between the first and second sensing parameter sets.

17. A method for managing HIS bundle pacing using an implantable medical device (IMD), the method comprising:
obtaining cardiac activity (CA) signals for a series of beats utilizing a candidate sensing configuration, the candidate sensing configuration defined by i) a HIS sensing vector that utilizes at least one HIS electrode and ii) a sensing channel that utilizes sensing circuitry configured to operate based on one or more sensing settings to detect near field and far field activity;
analyzing the CA signals to obtain an atrial (A) feature of interest (FOI) and a ventricular (V) FOI for corresponding beats within the series of beats;
identifying a V-A FOI relation between the A FOIs and the V FOIs across the series of beats;
adjusting the candidate sensing configuration between at least one of multiple HIS sensing vectors or multiple sensing settings, and repeating the obtaining, analyzing and identifying to obtain a collection of V-A FOI relations for a corresponding collect of candidate sensing configurations;
selecting a resultant sensing configuration from the collection of candidate sensing configurations based on one or more criteria; and
utilizing the resultant sensing configuration to manage the HIS bundle pacing during an atrial arrhythmia.

18. The method of claim 17, further comprising determining an A boundary for the A FOIs over the series of beats and a V boundary for the V FOIs over the series of beats.

19. The method of claim 18, wherein the determining further comprises determining a lowest value of the V FOIs collected over the series of beats, and an upper value of the A FOIs collected over the series of beats, the identifying the V-A FOI relation further comprising determining whether a ratio of the lowest value of the V FOIs and the upper value of the A FOIs exceed a predetermined threshold.

20. The method of claim 17, wherein the identifying the V-A FOI relation includes calculating a relation between at least one of means, means plus standard deviations, amplitudes or standard deviations between the V FOI and the A FOI.

21. The method of claim 17, further comprising locating the at least one HIS electrode in one of a right atrium or right ventricle proximate to the HIS bundle.

22. The method of claim 17, wherein the adjusting the candidate sensing configuration includes at least one of:
vii) switching the HIS sensing vector between at least two of a bipolar configuration, a unipolar configuration or an extended bipolar configuration;

viii) switching the HIS sensing vector between at least first and second combinations of the HIS electrode and additional electrodes; or ix) switching the sensing channel between first and second sensing settings.

23. The method of claim 17, wherein the adjusting the candidate sensing configuration further comprises switching the HIS sensing vector between first and second combinations of the HIS electrode and at least one additional electrode, the HIS electrode including at least one of a HIS tip electrode or a HIS ring electrode, the at least one additional electrode including at least two of an atrial ring electrode, an atrial tip electrode, a CAN electrode, a right ventricular electrode or a left ventricular electrode.

24. The method of claim 17, further comprising adjusting the candidate sensing configuration by switching between first and second sensing parameter sets.

* * * * *